United States Patent [19]

Terada et al.

[11] Patent Number: 5,262,420
[45] Date of Patent: Nov. 16, 1993

[54] PYRIDINE DERIVATIVES AND INSECTICIDE AND MITICIDE COMPRISING SAID DERIVATIVES

[75] Inventors: Izumi Terada; Katsuhiko Matsuzaki, both of Sodegaura; Kazuyoshi Nonoshita, Hiratsuka; Fumio Fujita, Yokohama, all of Japan

[73] Assignee: Idemitsu Kosan Co., Ltd., Tokyo, Japan

[21] Appl. No.: 886,300

[22] Filed: May 21, 1992

Related U.S. Application Data

[63] Continuation of Ser. No. 474,058, Apr. 17, 1990, filed as PCT/JP89/00882, Aug. 30, 1989, published as WO90/02736, Mar. 22, 1990, abandoned.

[30] Foreign Application Priority Data

Sep. 1, 1988 [JP] Japan .................................. 63-216256
Nov. 30, 1988 [JP] Japan .................................. 63-301011
Nov. 30, 1988 [JP] Japan .................................. 63-301012

[51] Int. Cl.⁵ .................... C07D 213/26; A01N 43/40
[52] U.S. Cl. ................................. 514/277; 546/346; 546/258; 546/263; 514/356
[58] Field of Search ............... 514/277, 356; 546/346, 546/258, 263

[56] References Cited

FOREIGN PATENT DOCUMENTS

| | | | |
|---|---|---|---|
| 1440647 | 4/1966 | France | 514/277 |
| 46-16106 | 5/1971 | Japan | 546/9 |
| 50-37657 | 4/1975 | Japan | 546/330 |
| 55-89266 | 7/1980 | Japan | 546/342 |
| 61-60651 | 3/1986 | Japan | 546/339 |

OTHER PUBLICATIONS

Eastman et al, J. Am. Chem. Soc., vol. 96, No. 7, pp. 2281-2283 apr. 3, 1974.
Pines et al., J. Org. Chem., vol. 34, No. 7, pp. 2113-2118 Jul. 1989.
Chemical Abstracts, vol. 80, No. 25, Abst. No. 145,973f Jun. 24, 1974.
Chemical Abstracts, vol. 81, No. 3, Abst. No. 12806c, Jul. 22, 1974.
Chemical Abstracts, vol. 84, No. 21, Abst. No. 150,258p May 24, 1976.
Chemical Abstracts, vol. 108, 1988, p. 642, abstract No. 94368z, Columbus, Ohio, US; E. Reimann et al: "Intramolecular alkylations of aromatic compounds. XVIII. Synthesis of 3,4-dihydro-1'-methylspiro[naphthalene-1(2H), 4'-piperidines]", Arch. Pharm. (Weinheim, Ger.) 1987, 320(5), 385-93.

Primary Examiner—Alan L. Rotman
Attorney, Agent, or Firm—Frishauf, Holtz, Goodman & Woodward

[57] ABSTRACT

A pyridine compound of the formula

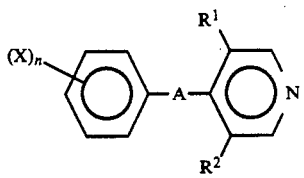

wherein X is a hydrogen atom, a halogen atom, an alkyl group having 1 to 4 carbon atoms, an alkoxyl group having 1 to 4 carbon atoms, a haloalkyl group having 1 to 4 carbon atoms or a haloalkoxyl group having 1 to 4 carbon atoms, n is 1 to 5, and when n is 2 or more, Xs may be identical to or different from each other, A is an alkyl residue or alkene residue in which a portion connecting the aryl group with the 4-position of the pyridyl group has 3 to 8 carbon atoms, or an alkapolyene residue in which said portion has 4 to 8 carbon atoms and 2 to 4 double bonds; the alkyl residue, alkene residue, and alkapolyene residue may have an alkyl side chain having 1 to 4 carbon atoms, an alkylidene side chain having 1 to 4 carbon atoms or 1 to 16 halogen atoms, and when there are 2 or more side chains, the side chains may be identical to or different from each other, and $R^1$ and $R^2$ are each a hydrogen atom or an alkyl group having 1 to 6 carbon atoms or salts thereof. The pyridine compounds and salts thereof exhibit a strong insecticidal and miticidal activity and are low in residuality and accumulativity and are thus useful as insecticides and miticides for the control of pests in agriculture and horticulture.

20 Claims, No Drawings

PYRIDINE DERIVATIVES AND INSECTICIDE AND MITICIDE COMPRISING SAID DERIVATIVES

This application is a continuation of application Ser. No. 07/474,058, filed Apr. 17, 1990, filed as PCT/JP89/00882, Aug. 30, 1989, published as WO90/02736, Mar. 22, 1990, abandoned.

TECHNICAL

The present invention relates to novel pyridine derivatives and the salts thereof, and an insecticide and miticide, and more particularly to pyridine derivatives and the salts thereof having an insecticidal and miticidal activity, and an insecticide and miticide comprising said derivatives or the salts thereof.

BACKGROUND ART

Insecticides have been used for controlling the noxious insects of agricultural and horticultural products, and controlling unsanitary insects, and thus have greatly contributed to increasing the yield of farm products and livestock products, and also to improvement in health environments. The conventional insecticides include chlorine-based, organophosphorus-based, carbamate-based, and pyrethroid-based insecticides. These insecticides, however, recently have met problems such as environmental pollution caused by drug application, problems in safety such as residuality or accumulativity, or problems in drug resistance. Under these circumstances, an insecticide and miticide having high effects and being free from the problems as above have been required to be developed.

Chemical Abstract 77 : 15609u describes that 1-phenyl-4-(4-pyridyl)-butane is used as herbicide, but makes no mention of its insecticidal property.

Japanese Patent Application Laid-Open No. 113715/1980 describes 1-phenyl-3-(4-pyridyl)-propane as the raw material of an antidepressant. J.O.C. 34,2113, 1969 reports compounds, in which the hydrogen of propylene group is substituted by an alkyl group in 1-phenyl-3-(4-pyridyl)propane, and further, J. Heterocycl. Chem. 24, 377, 1987 describes 1-phenyl-3-(4-pyridyl)-1-propane, of which a phenyl group is substituted by halogen or methoxycarbonyl group. In said literature, however, the physiological activity of these compounds are not described at all.

The present inventors have repeated extensive studies to develop a pyridine derivative having a high insecticidal and miticidal activity, and being free from the problems of residuality or accumulativity when used as an active ingredient of the insecticide and miticide.

As the result, it was found that pyridine derivatives having a specific structure and the salts thereof exhibit an excellent insecticidal and miticidal effect. The present invention has been accomplished based upon such knowledge.

The object of the present invention is to provide pyridine derivatives having a novel structure, and further to provide an insecticide and miticide comprising as an active ingredient, said pyridine derivatives of specific structure, having a high insecticidal and miticidal activity, and being very low in residuality and accumulativity.

DISCLOSURE OF INVENTION

The present invention provides novel pyridine derivatives represented by the general formula (I):

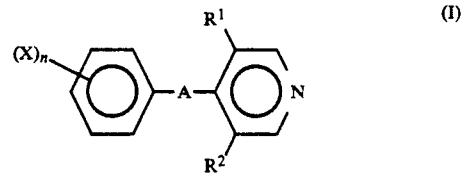

(wherein X is a hydrogen atom, a halogen atom, an alkyl group having 1 to 4 carbon atoms, an alkoxyl group having 1 to 4 carbon atoms, a haloalkyl group having 1 to 4 carbon atoms or a haloalkoxyl group having 1 to 4 carbon atoms. n is an integer of 1 to 5, and when n is 2 or more, Xs may be identical to or different from each other. A is an alkyl residue or alkene residue in which the portion connecting the aryl group with the 4-position of the pyridyl group has 3 to 8 carbon atoms, or an alkapolyene residue in which said portion has 4 to 8 carbon atoms and 2 to 4 double bonds. Said alkyl residue, alkene residue, and alkapolyene residue may have an alkyl side chain having 1 to 4 carbon atoms, an alkylidene side chain having 1 to 4 carbon atoms or 1 to 16 halogen atoms, and when they are 2 or more, they may be identical to or different from each other. Further, $R^1$ and $R^2$ are each a hydrogen atom or an alkyl group having 1 to 6 carbon atoms.

However, the following cases are excluded from the formula: (i) A is a propane residue and $R^1$ and $R^2$ are both hydrogen atoms, (ii) A is a propene residue and $R^1$ and $R^2$ are both hydrogen atoms, (iii) A is a butane residue and $R^1$ and $R^2$ are both hydrogen atoms, (iv) A is a butene residue and $R^1$ and $R^2$ are both hydrogen atoms, (v) A is a butadiene residue and $R^1$ and $R^2$ are both hydrogen atoms, and (vi) Xs are all hydrogen atoms and $R^1$ and $R^2$ are both hydrogen atoms. The invention also concerns the salts thereof, and the present invention provides an insecticide and miticide comprising as the active ingredient the pyridine derivatives represented by the general formula (I) or the salts thereof (including the cases (i) to (vi) mentioned above), being highly effective and free from the problems in residuality or accumulativity.

The novel pyridine derivative compounds provided in the present invention are represented by the general formula (i). In the formula (I), halogen atoms shown by X are chlorine, fluorine, bromine or iodine. The alkyl group having 1 to 4 carbon atoms shown by X may be either of straight chain or branched chain, and the specific examples of them are methyl, ethyl, n-propyl, isopropyl, n-butyl, isobutyl, s-butyl, t-butyl and the like. Alkoxyl groups having 1 to 4 carbon atoms shown by X include methoxyl, ethoxyl, n-propoxyl, isopropyl, n-butoxyl, isobutoxyl, t-butoxyl, and the like. A haloalkyl group having 1 to 4 carbon atoms shown by X means an alkyl group having 1 to 4 carbon atoms, in which at least one hydrogen atom in alkyl group is substituted by halogens, and the specific examples of them are monochloromethyl, dichloromethyl, trichloromethyl, monochloroethyl, dichloroethyl, trichloroethyl, tetrachloroethyl, monochloropropyl, dichloropropyl, trichloropropyl, tetrachloropropyl, pentachloropropyl, monochlorobutyl, dichlorobutyl, trichlorobutyl, tetrachlorobutyl, pentachlorobutyl, or hexachlorobutyl and the like, and, further, haloalkyl groups corresponding to the above-mentioned groups, in which at least one chlorine is substituted by fluorine, bromine and/or iodine.

A haloalkoxyl group having 1 to 4 carbon atoms indicated by X means an alkoxyl group in which at least one hydrogen of alkoxyl group having 1 to 4 carbon atoms is substituted by a halogen atom, and the examples of them are monochloromethoxyl, dichloromethoxyl, trichloromethoxyl, α-monochloroethoxyl, dichloroethoxyl, trichloroethoxyl, monochloropropoxyl, dichloropropoxyl, trichloropropoxyl, tetrachloropropoxyl, pentachloropropoxyl, monochlorobutoxyl, dichlorobutoxyl, trichlorobutoxyl, tetrachlorobutoxyl, pentachlorobutoxyl, or hexachlorobutoxyl group and the like, and haloalkoxyl groups corresponding to the above-described groups, in which haloalkoxyl groups one or plural chlorines are substituted by fluorine, bromine and/or iodine.

Therein, the number (n) of substituents indicated by X is 1 to 5, and when X is plural, that means, n is 2 or more, Xs may be identical to or different from each other.

The portion connecting the aryl group and the 4-position of pyridyl group indicated by A in the general formula (I) is an alkyl residue having 3 to 8 carbon atoms, an alkene residue having 3 to 8 carbon atoms, or an alkapolyene residue having 4 to 8 carbon atoms and having 2 to 4 double bonds.

Alkyl residues having 3 to 8 carbon atoms include propyl residue, butyl residue, pentyl residue, hexyl residue, heptyl residue, octyl residue and the like. Alkene residue having 3 to 8 carbon atoms means residue having double bonds in said carbon chains, and the position of the double bond is not critical.

Examples of said alkene residues are 1-propene residue, 1-butene residue, 2-butene residue, 1-pentene residue, 2-pentene residue, 1-hexene residue, 2-hexene residue, 1-heptene residue, 2-heptene residue, 1-octene residue, 2-octene residue and the like. Further, alkapolyene residue having 4 to 8 carbon atoms and having 2 to 4 double bonds means a residue having 2,3 or 4 double bonds in the said carbon chain, and the position of said double bond is not critical. However, those residues having neighboring double bonds are excluded. Examples of said groups are 1,3-butadiene residue, 1,3-pentadiene residue, 1,4-pentadiene residue, 1,3-hexadiene residue, 2,4-hexadiene residue, 1,4-hexadiene residue, 1,3-heptadiene residue, 2,4-heptadiene residue, 1,3-octadiene residue, 2,4-octadiene residue and the like.

A in the general formula (I) indicates a residue as mentioned above, and in addition, may have an alkyl group having 1 to 4 carbon atoms, an alkylidene group or halogen atoms as the side chain. Said side chain may exist in 1 to 16 in number, and may be identical to or different from each other. Therein, alkyl group having 1 to 4 carbon atoms and halogen atoms mean the above-described ones. Alkylidene group having 1 to 4 carbon atoms means those groups double-bonded to the main chain indicated as A, and the examples of them are methylidene, ethylidene, propylidene, butylidene and the like.

Further, $R^1$ and $R^2$ existing at 3- and 5-positions of the pyridine group represented by the general formula (I) are each a hydrogen or an alkyl group having 1 to 6 carbon atoms. An alkyl group having 1 to 6 carbon atoms may be straight chain or branched ones, and specific examples of them are methyl, ethyl, n-propyl, isopropyl, n-butyl, isobutyl, s-butyl, t-butyl, n-pentyl, isopentyl, neopentyl, t-pentyl, n-hexyl, isohexyl and the like. $R^1$ and $R^2$ may be identical to or different from each other.

In the pyridine derivatives represented by the general formula (I), when (i) A is propane residue and $R^1$ and $R^2$ are both hydrogen atoms, (ii) A is propene residue and $R^1$ and $R^2$ are both hydrogen atoms, (iii) A is butane residue and $R^1$ and $R^2$ are both hydrogen atoms, (iv) A is butene residue and $R^1$ and $R^2$ are both hydrogen atoms, (v) A is butadiene residue and $R^1$ and $R^2$ are both hydrogen atoms, and (vi) all the Xs are hydrogen atoms and $R^1$ and $R^2$ are both hydrogen atoms, such compounds are excluded from the novel pyridine derivatives of the present invention.

The pyridine derivatives represented by the general formula (I) above can be produced according to various methods. Specifically, when A is a substituted or unsubstituted propyl group having 3 carbon atoms, which means the compound is a pyridine derivative represented by the general formula (I'):

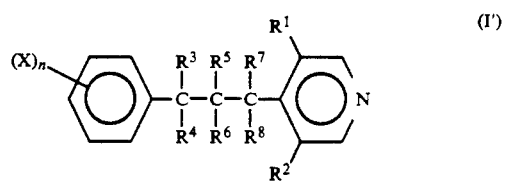

(wherein, X, n, $R^1$ and $R^2$ are as defined above, and $R^3$ to $R^8$ indicate the side chains of A) can be produced by addition reaction of a substituted phenethyl halide represented by the general formula (II):

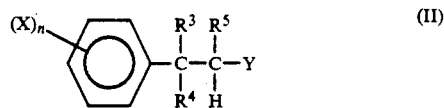

(wherein X, n, $R^3$, $R^4$ and $R^5$ are as defined above, and Y indicates a halogen atom) with a substituted pyridine represented by the general formula (III):

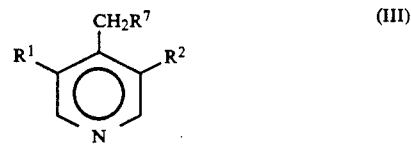

(wherein $R^1$, $R^2$ and $R^7$ are as defined above), in a solvent and in the presence of a base.

Examples of solvents to be used in the above reaction are, aromatic hydrocarbons such as benzene, toluene and the like; ethers such as diethylether, tetrahydrofuran, dimethoxyethane, and diglyme; polar aprotic solvents such as dimethylformamide, dimethylsulfoxide, hexamethyl phosphoric acid triamide; and liquid ammonia.

As the base, lithium diisopropylamine, t-butoxypotassium, phenylsodium, sodium amide and the like can be used.

Reaction conditions can be selected properly depending upon the circumstances, and reaction temperature is preferably $-100°$ C. to $50°$ C.

In the general formula (I), in order to substitute dialkyl group for α-carbon bonded at 4-position of pyridyl group, said substituted phenethyl halide represented by the general formula (II) is addition-reacted with the substituted pyridine represented by the general formula (IV):

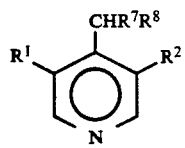

(IV)

(wherein R$^1$, R$^2$, R$^7$ and R$^8$ are as defined above). In that process, lithium aluminium hydride is used as the base, and other conditions should be arranged as in the addition reaction mentioned above.

When metallic sodium or potassium is added to the substituted pyridine represented by the general formula (IV), and reacted completely over 3 to 5 hours, to produce a metal compound represented by the general formula (V):

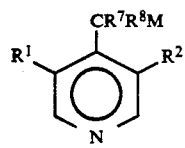

(V)

(wherein R$^1$, R$^2$, R$^7$ and R$^8$ are defined as above, and M indicates sodium or potassium), which is reacted with the compound represented by the general formula (VI):

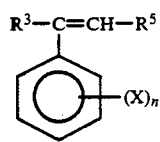

(VI)

(wherein X, n, R$^3$ and R$^5$ are as defined above), then the pyridine derivative represented by the general formula (I') wherein R$^4$ and R$^6$ are hydrogens can be produced. Said reaction proceeds rapidly at 0° to 25° C.

In order to produce the pyridine derivatives represented by the general formula (I') having two substituted side chains at the β-carbon in the carbon chain bonded to the 4-position of pyridyl group, the substituted phenethyl halide represented by the general formula (II'):

(II')

(wherein X, n, R$^3$, R$^4$, R$^5$, R$^6$ and Y are as defined above) is reacted, in the presence of magnesium, with the compound represented by the general formula (VII):

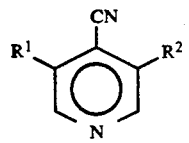

(VII)

(wherein R$^1$ and R$^2$ are as defined above), to produce the compound represented by the general formula (VIII):

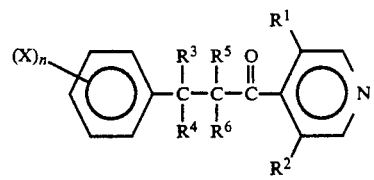

(VIII)

(wherein X, n, R$^1$, R$^2$, R$^3$, R$^4$, R$^5$ and R$^6$ are as defined above), and the resulting compounds is reduced with the use of hydrazine and alkali metal hydroxide and the like.

The above reaction is preferred to be carried out in solvents such as ethylene glycol, diethylene glycol, triethylene glycol and the like.

The conditions for the reaction can be selected properly according to the circumstances, and the reaction temperature is preferably 180° C. to 220° C.

Further, the pyridine derivatives in which A is an alkene residue having 3 carbon atoms and double bonds in the carbon chain, that means A is propenyl group, more specifically, pyridine derivatives represented by the general formula (I''):

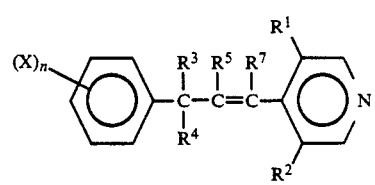

(I'')

(wherein X, n, R$^1$ to R$^5$ and R$^7$ are as defined above) can be produced according to the steps (a) to (c) as mentioned below including Grignard reaction. More specifically, (a) the substituted phenethyl halide represented by the general formula (II) is reacted with magnesium in a solvent, to produce a Grignard reagent represented by the general formula (IX):

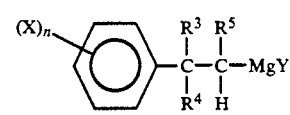

(IX)

(wherein X, n, R$^3$, R$^4$ and R$^5$ are as defined above, and Y is a halogen atom). The solvent to be used in the above reaction include ethers such as diethylether, tetrahydrofuran, and dimethoxyethane.

Other reaction conditions can be selected properly depending upon the circumstances. The preferred temperature is 30° to 80° C.

(b) The above Grignard reagent is reacted with pyridyl ketones represented by the general formula (X):

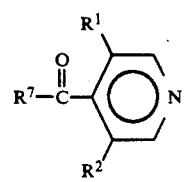

(X)

(wherein R$^1$, R$^2$ and R$^7$ are as defined above), to produce an alcoholic substance represented by the general formula (XI):

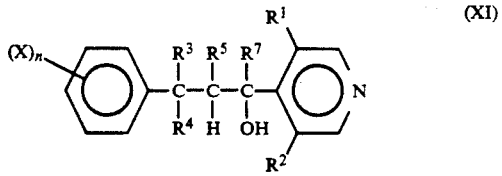

(wherein X, n, $R^1$ to $R^5$ and $R^7$ are as defined above). Said reaction is conducted in the same solvent as in step (a), in the temperature range of $-50°$ C. to $100°$ C., preferably $-10°$ C. to $20°$ C. Other reaction conditions can be selected properly according to the circumstances.

(c) The alcoholic substance obtained in the above-mentioned step (b) is dehydrated with the use of a dehydration agent in the presence or absence of solvent, to obtain the desired product of general formula (I″) having double bonds between the carbon bonded to the 4-position of pyridine and the adjacent carbon. Therein, aromatic solvents such as benzene, toluene, xylene, pyridine and the like can be used as the solvent, and dilute sulfuric acid, concentrated sulfuric acid, diphosphorus pentoxide, thionyl chloride, phosphorus oxichloride, phosphorus trioxide, phosphorus pentachloride and the like can be used as the dehydrating agent. Said dehydration reaction is usually effected at a temperature of $-30°$ C. to $150°$ C.

In order to obtain the desired product represented by the general formula (I″) having double bonds between the α-carbon bonded to 4-position of the pyridyl group and adjacent carbon, substituted phenyl acetic acid ester represented by the general formula (XII):

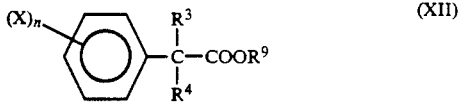

(wherein X, n, $R^3$ and $R^4$ are as defined above, and $R^9$ indicates an alkyl group) is subjected to a condensation reaction with the substituted pyridine represented by the general formula (III) in the presence of a base in a solvent, then the resulting ketone represented by the general formula (XIII):

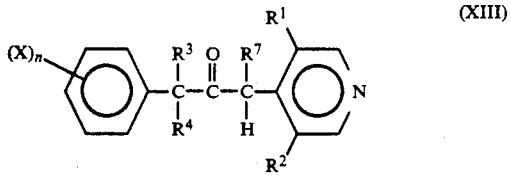

(wherein X, n, $R^1$ $R^2$, $R^3$, $R^4$ and $R^7$ are as defined above) is reduced, to obtain an alcoholic substance, which is dehydrated.

Examples of solvents to be used for the condensation reaction of the above-mentioned substituted phenyl acetic acid ester and substituted pyridine are aromatic hydrocarbons such as benzene, toluene and the like; ethers such as diethylether, tetrahydrofuran, dimethoxyethane, diglyme; polar aprotic solvents such as dimethylformamide, dimethylsulfoxide, hexamethyl phosphoric acid triamide; or liquid ammonia.

As the base, lithium diisopropylamine, t-butoxypotassium, phenyl sodium, sodium amide and the like can be used.

Reaction conditions can be selected properly according to the circumstances, and a preferred reaction temperature is $-100°$ C. to $50°$ C.

When alcohol is prepared from ketone, the catalysts to be used are sodium borohydride, sodium borocyanohydride, lithium aluminum hydride and the like.

The preferred solvents for the former two are tetrahydrofuran, ether and the like, and those for the latter are alcohols, alcohols containing water and the like. The reaction temperature in that process is preferably $0°$ to $70°$ C., more preferably $10°$ to $20°$ C.

The dehydration reaction of said alcohol is performed with the use of dilute sulfuric acid, concentrated sulfuric acid, diphosphorus pentaoxide, thionyl chloride, phosphorus oxychloride, phosphorus trichloride, phosphorus pentachloride and the like. Said reaction can be performed without a solvent, or in the presence of a aromatic solvent such as benzene, toluene, xylene, pyridine and the like.

Other conditions in the dehydration reaction can be selected properly according to the circumstances, but the preferable temperature is $-30°$ C. to $150°$ C.

Further, a pyridine derivative having double bonds between the β-carbon and γ-carbon in the carbon chain bonded to the 4-position of pyridyl group, that is, the compound represented by the general formula (I‴):

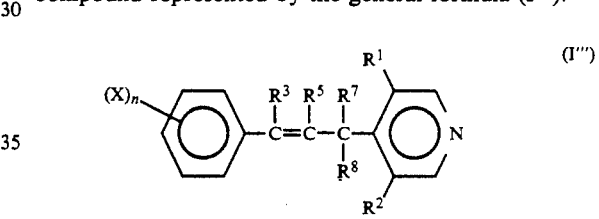

(wherein X, N, $R^1$, $R^2$, $R^3$, $R^5$, $R^7$ and $R^8$ are as defined above) is produced by subjecting the substituted epoxide represented by the general formula (XIV):

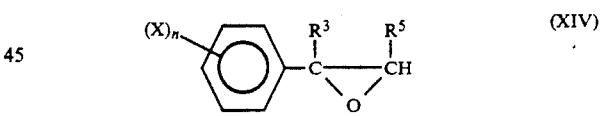

(wherein X, n, $R^3$ and $R^5$ are as defined above) to an addition reaction with the substituted pyridine of the above general formula (IV) in a solvent in the presence of a base, and by dehydrating the resulting alcohol represented by the general formula (XV):

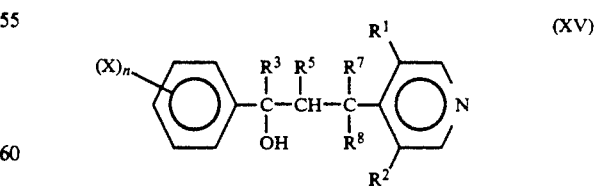

(wherein X, n, $R^1$, $R^2$, $R^3$, $R^5$, $R^7$ and $R^8$ are as defined above).

Solvents to be used in the addition reaction of the substituted epoxide and substituted pyridine are aromatic hydrocarbons such as benzene, toluene and the like, ethers such as diethylether, tetrahydrofuran, dimethoxy ethane, diglyme; polar aprotic solvents such as dimethylsulfoxide, hexamethyl phosphoric acid triamide; and liquid ammonia.

As the base, lithium diisopropylamine, t-butoxypotassim, phenyl sodium, sodium amide and the like can be used.

The conditions for the reaction can be selected properly according to the situation, and the preferable reaction temperature is −100° C. to 50° C.

The dehydration reaction of the alcoholic substance obtained by the above-described addition reaction is performed with the use of dilute sulfuric acid, concentrated sulfuric acid, diphosphorus pentaoxide, thionyl chloride, phosphorus oxychloride, phosphorus trichloride, phosphorus pentachloride and the like. The reaction may be carried out without a solvent, or in the presence of aromatic solvents such as benzene, toluene, xylene, pyridine and the like. Other conditions in the dehydration reaction may be selected properly according to the circumstances. The preferable temperature is −30° C. to 50° C.

When A is a substituted or unsubstituted propyl residue having 3 carbon atoms, the compound of the pyridine derivative of the general formula (I'), wherein $R^6$ and $R^8$ are hydrogen atoms can be produced by hydrogenating (I'') with the use of a hydrogenation catalyst usually used, and the compound of a pyridine derivative of (I') wherein $R^4$ and $R^6$ are hydrogen atoms can be produced by hydrogenating (I''') with the use of a hydrogenation catalyst usually used, respectively. Examples of the hydrogenating catalysts are palladium catalyst, nickel catalyst, molybdenum catalyst, platinum catalyst, and the like, and a particularly preferred one is palladium-carbon which is palladium supported on carbon.

The pyridine derivative of the present invention wherein A is a substituted or unsubstituted butane residue having 4 carbon atoms, specifically, the compound represented by the general formula (I''''):

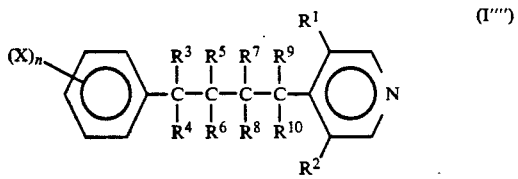

(wherein X, n, $R^1$ to $R^8$ are as defined above, and $R^9$ and $R^{10}$ are the side chain of A) can be produced by various processes. For example, the compound containing one substituent at the α-carbon bonded to 4-position of the pyridyl group can be produced by reacting a substituted phenylpropylhalide represented by the general formula (XVI):

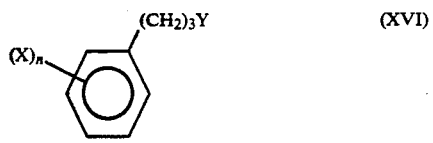

(wherein X and n are as defined above, and Y is a halogen atom) with the substituted pyridine represented by the general formula (III) in a solvent in the presence of a base. Examples of solvents to be used in the reaction are aromatic hydrocarbons such as benzene, toluene, and the like, ethers such as diethylether, tetrahydrofuran, dimethoxyethane, and diglyme, polar aprotic solvents such as dimethylformamide, dimethylsulfulfoxide, hexamethylphosphoric acid triamide and the like, or liquid ammonia.

As the base, lithium diisopropylamine, t-butoxy potassium, phenyl sodium, sodium amide and the like can be used.

The conditions for the reaction can be selected properly according to the circumstances. The reaction temperature is preferably −100° C. to 50° C.

In the general formula (I) mentioned before, the pyridine derivatives in which A is a unsubstituted, that is, butane residue can be produced by reacting a substituted phenyl propylhalide represented by the general formula (XVI) with the compound represented by the above-mentioned general formula (VII) in the presence of magnesium, to obtain a compound represented by the general formula (XVII):

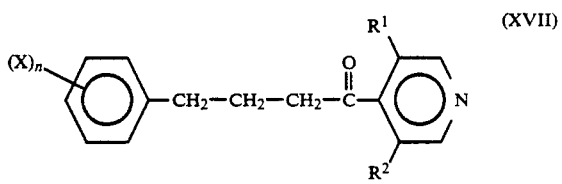

(wherein X, $R^1$, $R^2$ and n are as defined above), and then by reducing the resulting compound with the use of hydrazine and an alkali metal hydroxide and the like.

Said reaction should be carried out in a solvent such as ethylene glycol, diethylene glycol, triethylene glycol and the like.

Conditions for the reaction can be selected properly according to the circumstances, and the reaction temperature is preferably 180° C. to 220° C.

When A is an alkapolyene residue such as butadiene residue, having two double bonds and 4 carbon atoms, an aryl alkenyl aldehyde such as cinnamic aldehyde is subjected to an addition reaction with substituted a pyridine, to obtain an unsaturated alcohol, which is then dehydrated. Otherwise, said compound can be obtained by an addition-reaction of an aryl alkenyl epoxide with a substituted pyridine to obtain an unsaturated alcohol, and then dehydrating it.

Further, the compound of the present invention in which A has 5 to 8 carbon atoms can be produced with the use of the corresponding starting materials in the same manner as above.

It is also possible to react the compound of the general formula (I) in which X is hydrogen with alkylating agent or haloalkylating agent, to produce a compound wherein X is alkyl group or haloalkyl group. Said reaction can be carried out according to a conventional alkylating method or haloalkylating method.

Therein, alkylating agents include methylchloride, methylbromide, ethylchloride, ethybromide, i-propylchloride, i-propylbromide, t-butanol, t-butylchloride, t-butylbromide, sec-butylchloride, sec-butylbromide, 2-t-butyl-p-cresol, 2,6-di-t-butyl-p-cresol and the like. For example, when the reaction is carried out with 2,6-t-butyl-p-cresol dissolved into nitromethane in the presence of aluminum chloride as a catalyst, a pyridine derivative in which X is a t-butyl group in the above general formula (I) can be obtained.

Moreover, by using an alkylating agent, the methyl group on the pyridine ring can be extended.

Among the examples of pyridine derivatives of the present invention represented by the general formula (I) produced in the above process, the compounds in which A contains 3 carbon atoms are 1-(2-chlorophenyl)-3-(4-pyridyl)butane, 1-(2-fluorophenyl)-3-(4-pyridyl)-butane, 1-(3-chlorophenyl)-3-(4-pyridyl)-butane, 1-(3-trifluoromethylphenyl)-3-(4-pyridyl)-butane, 1-(4-fluorophenyl)-3-(4-pyridyl)-butane, 1-(4-chlorophenyl)-3-(4-pyridyl)-butane, 1-(4 methylphenyl)-3-(4-pyridyl)-butane, 1-(4-bromophenyl)-3-(4-pyridyl)-butane, 1-(2,4-dichlorophenyl)3-(4-pyridyl)-butane, 1-(3,4-dichlorophenyl)-3-(4-pyridyl)butane, 1-(2,6-dichlorophenyl) 3-(4-pyridyl)-butane, 1-phenyl-3-(3-ethyl-4-pyridyl)-propane, 1-phenyl-3-(3-ethyl-4-pyridyl)-butane, 1-phenyl-3-(3-methyl-4-pyridyl)-propane, 1-(2-chlorophenyl)-3-(3-ethyl-4-pyridyl) -propane, 1-(3-chlorophenyl)-3-(3-ethyl-4-pyridyl) -propane, 1-phenyl-3-(3-methyl-4-pyridyl)-butane, 1-phenyl-3-(3-n-propyl-4-pyridyl)butane, 1-phenyl-3-(4-pyridyl)-2-butene, 4-phenyl-2-(4-pyridyl)-1-butene, 1-(2-fluorophenyl)-3-(4-pyridyl)-2-butene, 2-phenyl-4-(4-pyridyl)-2-pentene, 1-phenyl-3 (3-n-butyl 4-pyridyl)-butane, 1-phenyl-3-(3-isobutyl-4-pyridyl)-butane, 1-phenyl-3-(3-n-hexyl-4-pyridyl)-butane, 1-(2-chlorophenyl)-3-(4-pyridyl)-propane, 1-(3-chlorophenyl)-3-(4-pyridyl)propane, 1-(4-chlorophenyl)-3-(4-pyridyl)-propane, 1-(3,4-dichloro-phenyl)-3-(4-pyridyl)-propane, 1-phenyl-3-(4-pyridyl)-butane, 1-(3-chlorophenyl)-3-(4-pyridyl)-propane, 1--(4-methoxyphenyl)-3-(4-pyridyl)-butane, 1-(4-pyridyl)-3-phenyl-butane, 1-phenyl-3-(4-pyridyl)-pentane, 1-phenyl-3-(4-pyridyl)-4-methylpentane, 1-(2-methylphenyl)-3-(3-ethyl-4-pyridyl)-propane, 1-(3 methylphenyl-3-(3-ethyl-4-pyridyl)propane, 1-(4-t-butylphenyl)-3-(3-ethyl-4-pyridyl)-propane, 1-(3-ethyl-4-pyridyl)-3-phenylbutane, 1-(3-chloro-4-methylphenyl)-3-(3-ethyl-4-pyridyl)-propane, 1-phenyl-3-(3-ethyl-4-pyridyl)-5-methylhexane, 1-phenyl-2-methyl-3-(3-ethyl-4-pyridyl)-propane and the like; compounds in which A contains 4 carbon atoms are 1-(2-fluorophenyl)-4-(4-pyridyl)butane, 1-(2-fluorophenyl)-4-(4-pyridyl)-pentane, 1-phenyl-4-(3-methyl-4-pyridyl)-butane, 1-phenyl-4-(3-ethyl-4-pyridyl)butane, 1-phenyl-4-(3-methyl-4-pyridyl)-pentane, 1-(2-chlorophenyl)-4-(3-ethyl-4-pyridyl)-butane, 1-(3-chlorophenyl)-4-(3-ethyl-4-pyridyl)-butane, 1-(4-chlorophenyl)-4-(3-ethyl-4-pyridyl)-butane, 1-phenyl-4-(4-pyridyl)-pentane, 1-(3-chlorophenyl)-4-(3-methyl-4-pyridyl)butane, 1-(3,4-dichlorophenyl)-4-(3-ethyl-4-pyridyl)-butane, 1-(3,4-dichlorophenyl)-4-(3-methyl-4-pyridyl)-pentane, 1-(3-trifluoromethylphenyl)-4-(3-ethyl-4-pyridyl)-butane, 1-(3-trifluoromethylphenyl)-4-(3-methyl-4-pyridyl)-pentane, 1-(4-t-butylphenyl)-4-(3-ethyl-4-pyridyl)-butane, 1-phenyl-4-(3-n-propyl-4-pyridyl)-pentane, 1-phenyl-4-(3-i-butyl-4-pyridyl)pentane, 1-phenyl-4-(3-ethyl-4-pyridyl)-hexane, 1-phenyl-4-(3-ethyl-4-pyridyl)-pentane, 1-phenyl-2-methyl-4-(3-ethyl-4-pyridyl)-1-butene, 1-phenyl-2-methyl-4-(3-ethyl-4-pyridyl)butane, 1-phenyl-2-methyl-4-(3-ethyl-4-pyridyl)-pentane, 1-(2-methylphenyl)-4-(3-ethyl-4-pyridyl)-butane, 1-(3-methylphenyl)-4-(3-ethyl-4-pyridyl)-butane, 1-(4-methylphenyl)-4-(3-ethyl-4-pyridyl)-butane, 1-(3-chloro-4-methylphenyl)-4-(3-ethyl-4-pyridyl)-butane, 1-phenyl-4-(3-methyl-4-pyridyl)-pentane, 1-(3-ethyl-4-pyridyl)-4-phenylpentane, 2-phenyl-3-methyl-5-(3-ethyl-4-pyridyl)-hexane, 1-phenyl-3-methyl-4-(3-ethyl-4-pyridyl)-hexane, 1-phenyl-4-(3-ethyl-4-pyridyl)-butane, 1-phenyl-3-methyl-4-(3-ethyl-4-pyridyl)-butane, 1-phenyl-4-(3-ethyl 4-pyridyl)-hexane, 1-phenyl-4-(4-pyridyl)-6-methylheptane, 2-phenyl-5-methyl-5-(4-pyridyl)-hexane, 1-phenyl-3-chloro-4-(3-ethyl-4-pyridyl)butane, 1-phenyl-3-methyl-4-(3 ethyl-4-pyridyl)-1,3-butadiene, 1-phenyl-4-methyl-4-(4-pyridyl) pentane, 1-phenyl-4-(3-ethyl-5-methyl-4-pyridyl)-butane, 1-phenyl-4-(3-methyl-5-propyl-4-pyridyl)-butane and the like; compounds in which A contains 5 carbon atoms are 1-phenyl 5 (4-pyridyl)-pentane, 1-phenyl-5-(4-pyridyl)-hexane, 1-phenyl-5-(3-methyl-4-pyridyl)-pentane, 1-phenyl-5-(3-ethyl-4-pyridyl)-pentane, 1-phenyl-5-(3-methyl-4-pyridyl)-hexane, 1-(2-chlorophenyl)-5-(3-ethyl-4-pyridyl)-pentane, 1-(3-chlorophenyl)-5-(3-ethyl-4-1-(4-chlorophenyl)-5-(3-ethyl-4-pyridyl)pentane and the like; compounds in which A contains 6 carbon atoms are 1-phenyl-6-(4-pyridyl)-hexane, 1-phenyl-6-(4-pyridyl)-heptane, 1-phenyl-6-(3-ethyl-4-pyridyl)-hexane and the like; compounds in which A contains 7 carbon atoms are 1-phenyl-7-(3-ethyl-4-pyridyl)-heptane and the like; and compounds in which A contains 8 carbon atoms are 1-phenyl-8-(3-ethyl-4-pyridyl)-octane, 1-phenyl-8-(3-ethyl-4-pyridyl)nonane and the like.

Said pyridine derivatives include stereoisomers in cis form (Z form) and trans form (E form), both of which have insecticidal and miticidal activity. Unless otherwise provided, in the present description, said pyridine derivatives shall include one of or both of these isomers.

The pyridine derivatives of the present invention can form, with an acid, pyridinium salts. Consequently, the present invention provides further the salts of pyridine derivatives. Examples of these acids are hydrochloric acid, hydrobromic acid, hydroiodic acid, hydrofluoric acid, sulfuric acid, phosphoric acid, nitric acid, citric acid, lactic acid, oxalic acid, maleic acid, tartaric acid, benzoic acid, nicotinic acid, dodecylbenzene sulfonic acid and the like.

The compounds of the pyridine derivatives of the present invention are the compounds specified above, and said pyridine derivatives and their salts have strong insecticidal and miticidal effects and also different structures from those of conventional insecticides. Accordingly, the former are considered to act on insects in a different mechanism of function from that of the latter.

The present invention provides an insecticide and miticide comprising the above-described pyridine derivative and the salt thereof as the active ingredient. Therein, said pyridine derivatives and the salts thereof are the compounds represented by the general formula (I):

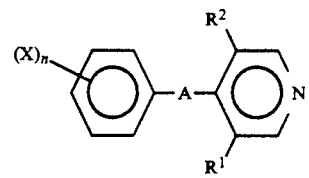

(wherein X, n, A, $R^1$ and $R^2$ are as defined above, and the compounds (i) to (vi) described before are also included).

The insects on which the pyridine derivatives (including the salts thereof) of the present invention exhibit activity are Hemiptera, Coleoptera, Lepidoptera, Acarina and the like. Typical examples of these insects are *Myzus persicae Aphis gossypii, Lipaphis erysimi, Nephotettix cincticeps, Nilaparvata lugens, Sogatella furcifera, Laodelphax striatellus, Trialeurodes vaporariorum,*

*Henosepilachna vigintioctopunctata, Oulema oryzae, Lissorhoptrus oryzophilus, Cnaphalocrocis medinalis, Tetranychus urticae, Panonychus citri* and the like.

The pyridine derivatives of the present invention are effective for controlling the insects growing in paddy fields (rice planthoppers including *Nilapatvata lugens, Sogatella furcifera*, and *Laodelphax striatellus*, or rice leafhoppers including *Nephotettix cincticeps*) which have recently caused problems since they have bred in a large number and because of the appearance of resistant varieties.

The pyridine derivatives of the present invention are effective for control of the noxious insects of wheat and barley, corn, vegetables, ornamentals, trees, cotton, fruit trees, lawn grass, pasture, harvested grains, wood, and woodproducts.

The insecticide and miticide of the present invention can be formed into solid, liquid or paste formulations containing the active ingredient, specifically, in the forms of dust, granule, fine granule, wettable powder, oil solution, emulsifiable concentrate, aerosol, flowable, and the like. Dust, a kind of solid formulation can be produced by blending the active ingredient with solid carrier, and grinding it. Granule or fine granule are produced by coating or impregnating the preformed granular solid carrier with the active ingredient, or combining the active ingredient to solid carriers by using cohesion techniques.

Examples of the solid carrier therein are vegetable powder including cereals, soybean, wood, bark, and bran; mineral powders such as clay, talc, bentonite, acid clay, kaolin, diatomaceous earth, synthetic silicate, pumice, active carbon, fly ash and the like; and synthetic resins.

Solid formulations may be in the form of dispersive or hydrous solid formulations including a wettable powder, in which besides the active ingredient and solid carrier, at least one surfactant active as a wetting agent, emulsifier, and/or dispersant is blended to improve the dispersion of the active ingredient into liquids.

Said surfactants include cationic, anionic, or nonionic surfactants. Cationic surfactants include quaternary ammonium salts, such as cetyltrimethylammonium bromide and the like. Anionic surfactants include alkylarylsulfonic acid salts, lignin sulfonic acid salts and the like, and nonionic surfactants include polyoxyethylene alkylaryl ethers, polyoxyethylene higher fatty acid esters, sorbitan esters, cane sugar esters and the like.

Liquid formulations comprise the solution or dispersion solution of the active ingredient in liquid a carrier, and in some cases, contain at least one kind of surfactant which acts as a wetting agent, emulsifier, and/or dispersant described above.

Liquid carriers include water, alcohols such as methanol, ethanol, ethylene glycol; ketones such as methyl ethyl ketone, diisobutyl ketone, and cyclohexanone; hydrocarbons such as kerosene, solvent naphtha, toluene, xylene; esters such as dioctylphthalate; amides such as dimethylformamide; nitriles such as acetonitorile; dimethyl sulfoxide; and oils and fats.

The insecticide and miticide of the present invention may contain, as adjuvants, stickers, thickeners, stabilizers, and said adjuvants include casein, gelatin, alginic acid, carboxymethyl cellulose, gum arabic, polyvinyl alcohol and the like.

The insecticide and miticide of the present invention may be a form of ready-to-use preparations, or a concentrated formulation to be diluted before use, and may contain 0.1 to 99% by weight, preferably 0.5 to 80% by weight of the pyridine derivative or the salt thereof of the present invention. For example, in the form of dust or granule, the pyridine derivative or the salt thereof of the present invention should be adequately contained in the amount of 0.5 to 20% by weight, and in the form of an emulsion or wettable powder, 5 to 50% by weight of said substance should be contained.

The examples of formulation in each form are as follows.

| Composition | Ratio (part by weight) |
|---|---|
| (a) Example of 50% emulsifiable concentrate | |
| Compound of the present invention | 50 |
| Xylene | 40 |
| Mixture of polyoxyethylene nonylphenyl ether and calcium alkylbenzene sulfonate | 10 |

Above components are uniformly stirred and blended to make an emulsifiable concentrate.

| (b) Example of 3% dust | |
|---|---|
| Compound of the present invention | 3 |
| Clay powder | 97 |

The above components are fully pulverized and blended to make a dust.

| (c) Example of 20% wettable powder | |
|---|---|
| Compound of the present invention | 20 |
| Anionic surfactant | 5 |
| Diatomaceous earth | 75 |

Above components are fully pulverized and blended to make a wettable powder.

| (d) Example of 2% oily solution | |
|---|---|
| Compound of the present invention | 2 |
| Kerosene | 98 |

Above components are uniformly blended to make an oil solution.

| (e) Example of 5% granule | |
|---|---|
| Compound of the present invention | 5 |
| Bentonite | 53 |
| Talc | 40 |
| Calcium lignine sulfonate | 2 |

Above components are fully pulverized and blended, kneaded sufficiently with addition of water, and after that, granulated, dried to make a granule.

The usual application rate of the insecticide and miticide of the present invention varies depending on various factors such as, type of target insect, condition and trend of emergence of pests, weather, form of the insecticidal preparation, mode of application, site to be applied, and time of the year. It is generally at a rate of 1 to 10 kg of formulation per 10 ares in the form of dust or granule. In case of emulsifiable concentrate or wettable powder to be applied in liquid form, it is diluted so that the concentration of the active ingredient may be not less than 0.001% by weight, to prepare a spray preparation.

The insecticide and miticide of the present invention can be applied in admixture with other conventional insecticides, miticides, insect hormone agents, fungicides, nematicides, herbicides, plant growth regulating agents, fertilizers and the like, to make multi-purpose compositions having excellent effects, and in addition synergistic effects of them can be expected.

Specific examples of insecticides to be blended are: pyrethroides such as permethrin, fenvalerate, esfenvalerate, cycloprothrin, bifenthrin, fenpropathrin, and etofenprox; organo-phosphorus such as Baycid, Elsan, diazinon, MEP, DDVP, malathion, dimethoate, DMTP, and acephate; carbamates such as NAC, MTMC, PHC, MPMC, BPMC, methomyl, carbosulfan, cartap, and oxamyl; benzoylureas such as chlorofluazuron, and teflubenzuron; in addition, fenbutatin oxide, amitraz, chlorobenzilate, fenoxycarb, and buprofezin.

Specific examples of fungicides are kasugamycin, blasticidin-S, fthalide, IBP, EDDP, tricyclazole, pyroquilon, isoprothiolane, validamycin, polyoxins, mepronil, flutolanil, pencycuron, diclomezine, thiophanate-methyl, procymidone, iprodione, triadimefon, bitertanol, fenarimol, prochloraz, triflumizole, pyrifenox, metalaxyl, fosetyl, and guazatine.

The present invention is described in greater detail with reference to the following examples and comparative examples.

EXAMPLE 1

Preparation of 1-(2-chlorophenyl)-3-(4-pyridyl)-butane

In a 200-ml flask, 0.94g (9.35 mmol) of diisopropyl amine and 15 ml of tetrahydrofuran were placed and cooled to $-50°$ C. Then 6.5 ml (10.3 mmol) of n-butyl lithium (15% n-hexane solution) was added thereto under nitrogen atmosphere. The resulting mixture was stirred for 10 minutes, and a solution of 1.0 g (9.35 mmol) of 4-ethylpyridine dissolved in tetrahydrofuran was added dropwise. After stirring for 30 minutes at $-50°$ C., the reaction temperature was gradually raised up to $-10°$ C., which was kept for 30 minutes, and lowered again to $-50°$ C. A solution of 2.05 g (9.35 mmol) of 2-chlorophenethyl bromide dissolved in tetrahydrofuran was added dropwise to the reaction mixture, and after stirring for 30 minutes at $-50°$ C., the temperature was raised up to room temperature. Subsequently, water was added, tetrahydrofuran was distilled away under reduced pressure, and the residue was extracted with ethyl acetate. The extract was washed with saturated brine, then dried over anhydrous sodium sulfate. Then, the solvent was distilled away under reduced pressure, to obtain an oil. Said oil was purified by silica gel column chromatography, to obtain 1.35 g of the desired compound (yield: 58.2%).

The resulting compound was identified as 1-(2-chlorophenyl)-3-(4-pyridyl)-butane (hereinafter referred to as compound 1) by melting point, infrared ray absorption spectrum (IR), nuclear magnetic resonance spectrum (NMR) and elementary analysis.

Oily substance at room temperature
IR(cm$^{-1}$):2900–3100, 1610, 1490
NMR(CDCl$_3$)$\delta$ (ppm):1.22, 3H, d; 1.6–2.1, 2H, m; 2.2–2.8, 3H, m; 6.8–7.3, 6H, m; 8.46, 2H, dd

| | Elementary Analysis (%) | | | |
|---|---|---|---|---|
| | C | H | Cl | N |
| Calculated | 73.31 | 6.56 | 14.43 | 5.70 |
| Found | 73.74 | 6.37 | 14.27 | 5.63 |

EXAMPLE 2

Preparation of 1-(2-fluorophenyl)-3-(4-pyridyl)-butane 1.0 g (9.35 mmol) of 4-ethylpyridine and 1.90 g (9.35 mmol) of 2-fluorophenethyl bromide were reacted in the same manner as in Example 1. The reaction product was purified, to obtain 0.74 g of desired compound (yield: 39.2%).

The resulting compound was identified as 1-(2-fluorophenyl)-3-(4-pyridyl)-butane (hereinafter referred to as compound 2) by the analytical results shown below.

Oily substance at room temperature
IR(cm$^{-1}$):2880–3080, 1600, 1500
NMR(CDCl$_3$) 6 (ppm):1.21, 3H, d; 1.65–2.15, 2H, m; 2.3–2.9, 3H, m; 6.6–7.3, 6H, m; 8.41, 2H, dd

| | Elementary Analysis (%) | | | |
|---|---|---|---|---|
| | C | H | F | N |
| Calculated | 78.57 | 7.03 | 8.29 | 6.11 |
| Found | 79.02 | 6.56 | 8.31 | 6.11 |

EXAMPLE 3

Preparation of 1-(3-chlorophenyl)-3-(4-pyridyl)-butane 1.0 g (9.35 mmol) of 4-ethylpyridine and 2.05 g (9.35 mmol) of 3-chlorophenethyl bromide were reacted in the same manner as in Example 1. The reaction product was purified to obtain 0.65 g of the desired compound (yield: 28.2%).

The resulting compound was identified as 1-(3-chlorophenyl)-3-(4-pyridyl)-butane (hereinafter referred to as compound 3) by the following analytical results.

Oily substance at room temperature
IR(cm$^{-1}$):2900–3100, 1610, 1490
NMR(CDCl$_3$)6 (ppm):1.22, 3H, d: 1.6–2.1, 2H, m; 2.2–2.8, 3H, m; 6.7–7.2, 6H, m; 8.39, 2H, dd

| | Elementary Analysis (%) | | | |
|---|---|---|---|---|
| | C | H | Cl | N |
| Calculated | 73.31 | 6.56 | 14.43 | 5.70 |
| Found | 73.72 | 6.12 | 46.46 | 5.70 |

EXAMPLE 4

Preparation of 1-(3-trifluoromethylphenyl)-3-(4-pyridyl)-butane 1.0 g (9.35 mmol) of 4-ethylpyridine and 2.37 g (9.35 mmol) of 3-trifluoromethylphenethyl bromide were reacted in the same manner as in Example 1. The reaction product was purified to obtain 0.40 g of the desired compound (yield: 15.3%).

The resulting compound was identified as 1-(3-trifluoromethylphenyl)-3-(4-pyridyl)-butane (hereinafter referred to as compound 4) by the following analytical results.

Oily substance at room temperature
IR(cm$^{-1}$) :2900–3100, 1615, 1510

NMR(CDCl₃)δ (ppm):1.23, 3H, d; 1.7-2.15, 2H, m; 2.2-3.25, 3H, m; 6.9-7.5, 6H, m; 8.35, 2H, dd

| | Elementary Analysis (%) | | | |
|---|---|---|---|---|
| | C | H | F | N |
| Calculated | 68.81 | 5.77 | 20.41 | 5.01 |
| Found | 68.65 | 5.70 | 20.60 | 5.05 |

EXAMPLE 5

Preparation of 1-(4-fluorophenyl)-3-(4-pyridyl)-butane 1.0 g (9.35 mmol) of 4-ethylpyridine and 1.90 g (9.35 mmol) of 4-fluorophenethyl bromide were reacted in the same manner as in Example 1. The reaction product was purified to obtain 1.67 g of the desired compound (yield: 77.9%). The resulting compound was identified as 1-(4-fluorophenyl)-3-(4-pyridyl)-butane (hereinafter referred to as compound 5) by the following analytical results.

Oily substance at room temperature
IR(cm⁻¹):2880-3100, 1608, 1520
NMR(CDCl₃) δ (ppm):1.20, 3H, d; 1.5-2.1, 2H, m; 2.2-2.9, 3H, m; 6.9-7.4, 6H, m; 8.43, 2H, dd

| | Elementary Analysis (%) | | | |
|---|---|---|---|---|
| | C | H | F | N |
| Calculated | 78.57 | 7.03 | 8.29 | 6.11 |
| Found | 78.67 | 6.84 | 8.36 | 6.14 |

EXAMPLE 6

Preparation of 1-(4-chlorophenyl)-3-(4-pyridyl)-butane 1.0 g (9.35 mmol) of 4-ethylpyridine and 2.05 g (9.35 mmol) of 4-chlorophenethyl bromide were reacted in the same manner as in Example 1. The reaction product was purified to obtain 1.37 g of the desired compound (yield: 59.8%).

The resulting compound was identified as 1-(4-chlorophenyl)-3-(4-pyridyl)-butane (hereinafter referred to as compound 6) by the following analytical results.

Oily substance at room temperature
IR(cm⁻¹):2870-3100, 1605, 1500
NMR(CDCl₃)δ (ppm):1.20, 3H, d; 1.6-2.05, 2H, m; 2.2-2.85, 3H, m; 6.7-7.3, 6H, m; 8.41, 2H, dd

| | Elementary Analysis (%) | | | |
|---|---|---|---|---|
| | C | H | Cl | N |
| Calculated | 73.31 | 6.56 | 14.43 | 5.70 |
| Found | 73.36 | 6.38 | 14.54 | 5.72 |

EXAMPLE 7

Preparation of 1-(4-methylphenyl)-3-(4-pyridyl)-butane 1.0 g (9.35 mmol) of 4-ethylpyridine and 1.86 g (9.35 mmol) of 4-methylphenethyl bromide were reacted in the same manner as in Example 1. The reaction product was purified to obtain 2.07 g of the desired compound (yield: 98.4%). The resulting compound was identified as 1-(4-methylphenyl)-3-(4-pyridyl)-butane (hereinafter referred to as compound 7) by the following analytical results.

Oily substance at room temperature
IR(cm⁻¹):2850-3050, 1600, 1518
NMR(CDCl₃)δ (ppm):1.17, 3H, d; 1.6-2.05, 3H, m; 2.22, 3H, s; 2.2-2.8, 3H, m; 6.8-7.1, 6H, m; 8.37, 2H, dd

| | Elementary Analysis (%) | | |
|---|---|---|---|
| | C | H | N |
| Calculated | 85.29 | 8.50 | 6.22 |
| Found | 85.14 | 8.63 | 6.24 |

EXAMPLE 8

Preparation of 1-(4-bromophenyl)-3-(4-pyridyl)-butane 1.0 g (9.35 mmol) of 4-ethylpyridine and 2.47 g (9.35 mmol) of 4-bromophenethyl bromide were reacted in the same manner as in Example 1. The reaction product was purified to obtain 1.10 g of the desired compound (yield: 40.7%).

The resulting compound was identified as 1-(4-bromophenyl)-3-(4-pyridyl)-butane (hereinafter referred to as compound 8) by the following analytical results.

Oily substance at room temperature
IR(cm⁻¹):2900-3100, 1610, 1500
NMR(CDCl₃)δ (ppm):1.30, 3H, d; 1.6-2.1, 2H, m; 2.25-2.9, 3H, m; 6.85, 2H, d; 6.97, 2H, dd; 7.28, 2H, d; 8.39, 2H, dd

| | Elementary Analysis (%) | | | |
|---|---|---|---|---|
| | C | H | Br | N |
| Calculated | 62.08 | 5.56 | 27.53 | 4.83 |
| Found | 62.56 | 5.40 | 27.27 | 4.78 |

EXAMPLE 9

Preparation of 1-(2,4-dichlorophenyl)-3-(4-pyridyl)butane 1.0 g (9.35 mmol) of 4-ethylpyridine and 2.37 g (9.35 mmol) of 2,4-dichlorophenethyl bromide were reacted in the same manner as in Example 1. The reaction product was purified to obtain 0.67 g of the desired compound (yield: 25.6%). The resulting compound was identified as 1-(2,4-dichlorophenyl)-3-(4-pyridyl)-butane (hereinafter referred to as compound 9) by the following analytical results.

Oily substance at room temperature
IR(cm⁻¹):2900-3100, 1620, 1495
NMR(CDCl₃)δ (ppm):1.24, 3H, d; 1.6 2.1, 2H, m; 2.3-2.9, 3H, m; 7.0-7.3, 5H, m; 8.43, 2H, dd

| | Elementary Analysis (%) | | | |
|---|---|---|---|---|
| | C | H | Cl | N |
| Calculated | 64.30 | 5.40 | 25.31 | 5.00 |
| Found | 64.28 | 5.26 | 25.44 | 5.02 |

EXAMPLE 10

Preparation of 1-(3,4-dichlorophenyl)-3-(4-pyridyl)butane 1.0 g (9.35 mmol) of 4-ethylpyridine and 2.37 g (9.35 mmol) of 3,4-dichlorophenethyl bromide were reacted in the same manner as in Example 1. The reaction product was purified to obtain 1.17 g of the desired compound (yield: 44.6%).

The resulting compound was identified as 1-(3,4-dichlorophenyl)-3-(4-pyridyl)-butane (hereinafter referred to as compound 10) by the following analytical results.

Oily substance at room temperature
IR(cm$^{-1}$):2900–3100, 1610, 1482
NMR(CDCl$_3$)δ (ppm):1.23, 3H, d; 1.6–2.1, 2H, m; 2.2–2.9, 3H, m; 6.7–7.35, 5H, m; 8.44, 2H, dd

|  | Elementary Analysis (%) | | | |
| --- | --- | --- | --- | --- |
|  | C | H | Cl | N |
| Calculated | 64.30 | 5.40 | 25.31 | 5.00 |
| Found | 64.77 | 5.23 | 25.05 | 4.95 |

EXAMPLE 11

Preparation of 1-(2,6-dichlorophenyl)-3-(4-pyridyl)butane 1.0 g (9.35 mmol) of 4-ethylpyridine and 2.37 g (9.35 mmol) of 2,6-dichlorophenethyl bromide were reacted in the same manner as in Example 1. The reaction product was purified to obtain 1.45 g of the desired compound (yield: 55.3%). The resulting compound was identified as 1-(2,6-dichlorophenyl)-3-(4-pyridyl)-butane (hereinafter referred to as compound 11) by the following analytical results.

Oily substance at room temperature
IR(cm$^{-1}$):2900–3100, 1610, 1505
NMR(CDCl$_3$)δ (ppm):1.26, 3H, d; 1.5–2.1, 2H, m; 2.4–3.0, 3H, m; 6.7–7.35, 5H, m; 8.42, 2H, dd

|  | Elementary Analysis (%) | | | |
| --- | --- | --- | --- | --- |
|  | C | H | Cl | N |
| Calculated | 64.30 | 5.40 | 25.31 | 5.00 |
| Found | 64.64 | 5.06 | 25.31 | 5.00 |

EXAMPLE 12

Preparation of 1-phenyl-3-(3-ethyl-4-pyridyl)-propane 1.13 g (9.35 mmol) of 3-ethyl-4-methylpyridine and 1.73 g (9.35 mmol) of phenethyl bromide were reacted in the same manner as in Example 1. The reaction product was purified to obtain 1.95 g of the desired compound (yield: 92.8%). The resulting compound was identified as 1-phenyl-3-(3-ethyl-4-pyridyl)-propane (hereinafter referred to as compound by the following analytical results.

Oily substance at room temperature
IR(cm$^{-1}$):2900–3100, 1600, 1502
NMR(CDCl$_3$) δ (ppm):1.20, 3H, t; 1.5–2.2, 2H, m; 2.25–2.8, 6H, m; 6.88, 1H, d; 7.10, 5H, br s; 8.21, 1H, d; 8.25, 1H, s

|  | Elementary Analysis (%) | | |
| --- | --- | --- | --- |
|  | C | H | H |
| Calculated | 85.29 | 8.50 | 6.22 |
| Found | 85.28 | 8.45 | 6.27 |

EXAMPLE 13

Preparation of 1-phenyl-3-(3-ethyl-4-pyridyl)-butane 1.26 g (9.35 mmol) of 3,4-diethylpyridine and 1.73 g (9.35 mmol) of phenethyl bromide were reacted in the same manner as in Example 1. The reaction product was purified to obtain 1.28 g of the desired compound (yield: 57.2).

The resulting compound was identified as 1-phenyl-3-(3-ethyl-4-pyridyl)-butane (hereinafter referred to as compound 13) by the following analytical results.

Oily substance at room temperature
IR(cm$^{-1}$):2900–3100, 1607, 1510
NMR(CDCl$_3$) δ (ppm):1.14, 3H, t; 1.24, 3H, d; 1.7–2.1, 2H, m; 2.3–3.2, 5H, m; 6.9–7.4, 6H, m; 8.35, 1H, s; 8.38, 1H, d

|  | Elementary Analysis (%) | | |
| --- | --- | --- | --- |
|  | C | H | H |
| Calculated | 85.31 | 8.84 | 5.85 |
| Found | 85.58 | 8.62 | 5.80 |

EXAMPLE 14

Preparation of 1-phenyl-3-(3-methyl-4-pyridyl)-propane 1.0 g (9.35 mmol) of 3,4-dimethylpyridine and 1.73 g (9.35 mmol) of phenethyl bromide were reacted in the same manner as in Example 1. The reaction product was purified to obtain 1.82 g of the desired compound (yield: 92.4%).

The resulting compound was identified as 1-phenyl-3-(3-methyl-4-pyridyl)-propane (hereinafter referred to as compound 14) by the following analytical results.

Oily substance at room temperature
IR(cm$^{-1}$):2880–3100, 1600, 1505
NMR(CDCl$_3$) (ppm):1.7–2.1, 2H, m; 2.20, 3H, s; 2.45–2.8, 4H, m; 7.02, 1H, d; 7.1–7.45, 5H, m; 8.2–8.4, 2H, m

|  | Elementary Analysis (%) | | |
| --- | --- | --- | --- |
|  | C | H | H |
| Calculated | 85.26 | 8.11 | 6.63 |
| Found | 85.58 | 7.88 | 6.54 |

EXAMPLE 15

Preparation of 1-(2-chlorophenyl)-3-(3-ethyl-4-pyridyl)-propane 1.13 g (9.35 mmol) of 3-ethyl-4-methylpyridine and 2.05 g (9.35 mmol) of 2-chlorophenethyl bromide were reacted in the same manner as in Example 1. The reaction product was purified to obtain 1.04 g of the desired compound (yield: 42.8%).

The resulting compound was identified as 1-(2-chlorophenyl)-3-(3-ethyl-4-pyridyl)-propane (hereinafter referred to as compound 15) by the following analytical results.

Oily substance at room temperature
IR(cm$^{-1}$):2860–3050, 1590, 1470
NMR(CDCl$_3$)δ (ppm):1.20, 3H, t; 1.7–2.15, 2H, m; 2.4–2.9, 6H, m; 7.0–7.4, 5H, m; 8.33, 1H, d; 8.36, 1H, s

| Elementary Analysis (%) | | | | |
|---|---|---|---|---|
| | C | H | Cl | N |
| Calculated | 73.98 | 6.98 | 13.65 | 5.39 |
| Found | 74.29 | 6.96 | 13.44 | 5.31 |

EXAMPLE 16

Preparation of 1-(3-chlorophenyl)-3-(3-ethyl-4-pyridyl)-propane 1.13 g (9.35 mmol) of 3-ethyl-4-methylpyridine and 2.05 g (9.35 mmol) of m-chlorophenethyl bromide were reacted in the same manner as in Example 1. The reaction product was purified to obtain 1.23 g of the desired compound (yield: 50.7%).

The resulting compound was identified as 1-(3-chlorophenyl)-3-(3-ethyl-4-pyridyl)-propane (hereinafter referred to as compound 16) by the following analytical results.

Oily substance at room temperature
IR(cm$^{-1}$):2880-3070, 1600, 1485
NMR(CDCl$_3$)$\delta$ (ppm):1.20, 3H, t; 1.7-2.15, 2H, m; 2.4-2.9, 6H, m; 6.9-7.35, 5H, m; 8.33, 1H, d; 8.37, 1H, s

| Elementary Analysis (%) | | | | |
|---|---|---|---|---|
| | C | H | Cl | N |
| Calculated | 73.98 | 6.98 | 13.65 | 5.39 |
| Found | 74.37 | 6.43 | 13.77 | 5.43 |

EXAMPLE 17

Preparation of 1-phenyl-3-(3-methyl-4-pyridyl)-butane 1.13 g (9.35 mmol) of 3-methyl-4-ethylpyridine and 1.73 g (9.35 mmol) of phenethyl bromide were reacted in the same manner as in Example 1. The reaction product was purified to obtain 1.36 g of the desired compound (yield: 64.5%).

The resulting compound was identified as 1-phenyl-3-(3-methyl-4-pyridyl)-butane (hereinafter referred to as compound 17) by the following analytical results.

Oily substance at room temperature
IR(cm$^{-1}$):2890-3090, 1602, 1504
NMR(CDCl$_3$)$\delta$ (ppm):1.22, 3H, d; 1.7-2.1, 2H, m; 2.18, 3H, s; 2.4-3.1, 3H, m; 7.0-7.4, 6H, m; 8.34, 1H, s; 8.39, 1H, d

| Elementary Analysis (%) | | | |
|---|---|---|---|
| | C | H | N |
| Calculated | 85.29 | 8.50 | 6.22 |
| Found | 85.07 | 8.79 | 6.14 |

EXAMPLE 18

Preparation of 1-phenyl-3-(3-n-propyl-4-pyridyl)butane 2.1 g (9.35 mmol) of 1-phenyl-3-(3-methyl-4-pyridyl)-butane, 1.46 g (9.35 mmol) of ethyl iodide and 2 equivalent of lithium-diisopropylamine were reacted in the same manner as in Example 1. The reaction product was purified to obtain 0.37 g of the desired compound (yield: 15.6%).

The resulting compound was identified as 1-phenyl-3-(3-n-propyl-4-pyridyl)-butane (hereinafter referred to as compound 18) by the following analytical results.

Oily substance at room temperature
IR(cm$^{-1}$):2890-3100, 1600, 1500
NMR(CDCl$_3$)$\delta$ (ppm):0.88, 3H, t; 1.21, 3H, d; 1.3-2.05, 4H, m; 2.2-2.7, 4H, m; 2.8-3.15, 1H, m; 7.0-7.45, 6H, m; 8.30, 1H, s; 8.35, 1H, d

| Elementary Analysis (%) | | | |
|---|---|---|---|
| | C | H | N |
| Calculated | 85.32 | 9.15 | 5.53 |
| Found | 85.17 | 9.07 | 5.76 |

EXAMPLE 19

Preparation of (E)-1-phenyl-3-(4-pyridyl)-2-butene and 4-phenyl-2-(4-pyridyl)-1-butene In a three-necked flask, 0.4 g (16.2 mmol) of powdered magnesium and 10 ml of dried ether were placed and a solution of 3.0 g (16.2 mmol) of phenetyl bromide dissolved in ether was gradually added dropwise under a nitrogen atmosphere. Since ether began to reflux when the reaction began, phenetyl bromide was added so as to continue refluxing. After the dropwise addition was over, the mixture was kept-refluxing for one hour and then, cooled on an ice bath, and added was a solution of 1.78 g (14.8 mmol) of 4-acetylpyridine dissolved in ether. After stirring for 30 minutes, ice bath was removed and refluxing was kept for another one hour. After cooling, 5% ammonium chloride was added and the mixture was extracted with ether and the organic layer was washed with 5% hydrochloric acid twice. The aqueous layer was alkalized with sodium carbonate and extracted with ethyl acetate. Organic layers were mixed and dried over anhydrous sodium sulfate. Ethyl acetate was distilled away under reduced pressure to obtain 1.42 g (42.4%) of alcoholic substance.

To the said alcoholic substance, that is 1.42 g of 2-(4-pyridyl)-4-phenyl-2-butanol, 4 ml of 65% sulfuric acid was added and the mixture was stirred for two hours at 100° C. After cooling, water was added and the mixture was alkalized with sodium carbonate to extract with ethyl acetate. After drying over anhydrous sodium sulfate, the solvent was distilled away under reduced pressure to obtain viscous oily substance. The said oily substance was purified by silica gel column chromatography to obtain 0.44 g of (E)-1-phenyl-3-(4-pyridyl)-2-butene (yield: 33.7%) and 0.15 g of 4-phenyl-2-(4-pyridyl)-1-butene (yield: 11.5%).

The resulting compound was identified as (E)-1-phenyl-3-(4-pyridyl)-2-butene (hereinafter referred to as compound 19) and 4-phenyl-2-(4-pyridyl)-1-butene (hereinafter referred to as compound 20) by the following analytical results.

compound 19
Oily substance at room temperature
IR(cm$^{-1}$):2880-3080, 1652, 1600, 1504
NMR(CDCl$_3$)$\delta$ (ppm):2.04, 3H, s; 3.48, 2H, d; 6.07, br t, 7.0-7.3 7H, m; 8.41, 2H, dd

| Elementary Analysis (%) | | | |
|---|---|---|---|
| | C | H | N |
| Calculated | 86.08 | 7.22 | 6.69 |

-continued

| | Elementary Analysis (%) | | |
|---|---|---|---|
| | C | H | N |
| Found | 86.42 | 6.98 | 6.60 |

Compound 20
Oily substance at room temperature
IR(cm$^{-1}$):2880–3080, 1640, 1602, 1504
NMR(CDCl$_3$)δ (ppm):2.70, 4H, s; 5.1, 1H, s; 5.39, 1H, s; 6.9–7.3, 7H, m; 8.43, 2H, dd

| | Elementary analysis (%) | | |
|---|---|---|---|
| | C | H | N |
| Calculated | 86.08 | 7.22 | 6.69 |
| Found | 85.68 | 7.62 | 6.70 |

EXAMPLE 20

Preparation of
(Z)-1-(2-fluorophenyl)-3-(4-pyridyl)-2-butene

In a 200-ml flask, 5.2 g (11.8 mmol) of diisopropylamine and 40 ml of tetrahydrofuran were placed and cooled to −50° C. Then, 34 ml (56 mmol) of n-butyl lithium (15% n-hexane solution) was added thereto under a nitrogen atmosphere. The resulting mixture was stirred for 10 minutes, and a solution of 5.0 g (55.8 mmol) of 4.methylpyridine dissolved in tetrahydrofuran was added dropwise. After stirring for 30 minutes at −50° C., the reaction temperature was gradually raised up to −10° C., which was kept for 30 minutes, and lowered again to −50° C. A solution of 7.7 g (42.3 mmol) of ethyl-o-fluorophenyl acetate dissolved in tetrahydrofuran was added dropwise thereto, and after stirring for 30 minutes at −50° C., the temperature was returned to room temperature. Subsequently, water was added, tetrahydrofuran was distilled away under reduced pressure, the residue was extracted with ethyl acetate, washed with saturated brine and dried over anhydrous sodium acetate. The solvent and 4-ethylpyridine were distilled away under reduced pressure to obtain 6.17 g of oily substance (yield: 60.0%). To the said oily substance, that is 1.65 g (6.79 mmol) of 1-(2-fluorophenyl)-3-(4-pyridyl)-butane-2-one was dissolved in 10 ml of methanol and 130 mg of sodium borohydride was added little by little. After adding all the quantity, the mixture was stirred for one hour at room temperature and excessive sodium borohydride was decomposed by adding 10 ml of 5% hydrochloric acid. Methanol was distilled away under reduced pressure and the residue was alkalized with sodium carbonate and was extracted with ethyl acetate. After drying over anhydrous sodium sulfate, ethyl acetate was distilled away under reduced pressure to obtain 1.59 g of white solid (yield: 95.6%).

To the said solid, that is, 1.59 g (6.49 mmol) of 1-(2-fluorophenyl)-3-(4-pyridyl)-2-butanol, 2.5 ml of thionyl chloride was added and stirred for one hour at 40° C. After distilling away excessive thionyl chloride under reduced pressure, water was added and the residue was alkalized with sodium carbonate and was extracted with ethyl acetate. After drying over anhydrous sodium sulfate, ethyl acetate was distilled away under reduced pressure to obtain a brown oily substance. The resulting oily substance was purified by silica gel column chromatography to obtain 0.54 g of the desired compound (yield: 31.6%).

The resulting compound was identified as (Z)-1-(2-fluorophenyl)-3-(4-pyridyl)-2-butene (hereinafter referred to as compound 21) by the following analytical results.

Oily substance at room temperature
IR(cm$^{-1}$):2870–3100, 1604, 1500
NMR(CDCl$_3$)δ (ppm):1.99, 3H, br s, 3.27, 2H, d; 5.67, 1H, br t, 6.7–7.4, 6H, m; 8.51, 2H, dd

| | Elementary analysis (%) | | | |
|---|---|---|---|---|
| | C | H | F | N |
| Calculated | 79.27 | 6.21 | 8.36 | 6.16 |
| Found | 79.67 | 5.99 | 8.27 | 6.08 |

EXAMPLE 21

Preparation of (E)-2-phenyl-4-(4-pyridyl)-2-pentene
and (Z)-2-phenyl-4-(4-pyridyl)-2-pentene In a 200-ml flask, 3.74 g (37.0 mmol) of diisopropylamine and 30 ml of tetrahydrofuran were placed and cooled to −50° C. Then, 25.6 ml (12.9 mmol) of n-butyl lithium (15% n-hexane solution) was added thereto under a nitrogen atmosphere. The resulting mixture was stirred for 10 minutes, and a solution of 4.0 g (43.0 mmol) of 4-ethylpyridine dissolved in tetrahydrofuran was added dropwise. After stirring for 30 minutes at −50° C., the reaction temperature was gradually raised up to −10° C., which was kept for 30 minutes, and lowered again to −50° C. A solution of 5.0 g (37.0 mmol) of 2-phenylpropyrene oxide dissolved in tetrahydrofuran was added dropwise to the reaction mixture, and after stirring for 30 minutes at −50° C., the temperature was returned to room temperature. Subsequently, water was added, tetrahydrofuran was distilled away under reduced pressure, the residue was extracted with ethyl acetate and was washed with saturated brine and dried over anhydrous sodium acetate. The solvent was distilled away under reduced pressure to obtain 8.83 g of oily substance (yield: 98.9%).

To the said oily substance, that is , 8.83 g (36.6 mmol) of 2-phenyl-4-(4-pyridyl)-2-pentanol, 15 ml of 65% sulfuric acid was added and the mixture was heated for 2 hours at 100° C and after cooling, water was added. The mixture was alkalized with sodium carbonate and was extracted with ethyl acetate. Subsequently, layer a of ethyl acetate was dried over anhydrous sodium sulfate and the solvent was distilled away under reduced pressure and purified by silica gel column chromatography to obtain 0.45 g of (E)-2-phenyl-4-(4-pyridyl)-2-pentene (yield: 17%) and 0.10 g of (Z)-2-phenyl-4-(4-pyridyl)-2-pentene (yield: 4%).

The resulting compound was identified as (E)-2-phenyl-4-(4-pyridyl)-2-pentene (hereinafter referred to as compound 22) and (Z)-2-phenyl-4-(4-pyridyl)-2-pentene (hereinafter referred to as compound 23) by the following analytical results.

Compound 22
Oily substance at room temperature
IR(cm$^{-1}$):2880–3060, 1598, 1498
NMR(CDCl$_3$)δ (ppm):1.28, 3H, d; 1.96, 3H, br s, 3.4–4.1, 1H, m; 5.77, 1H, br d, 6.7–7.4, 7H, m; 8.37, 1H, dd

| Elementary analysis (%) | | | |
|---|---|---|---|
| | C | H | N |
| Calculated | 86.06 | 7.67 | 6.27 |
| Found | 86.23 | 7.61 | 6.16 |

Compound 23
Oily substance at room temperature
IR(cm$^{-1}$):2870-3070, 1604, 1501
NMR(CDCl$_3$)$\delta$ (ppm):1.23, 3H d; 2.00, 3H, br s, 3.1-3.65, 1H, m; 5.43, 1H, br d, 6.8-7.3, 7H, m; 8.31, 1H, dd

| Elementary Analysis (%) | | | |
|---|---|---|---|
| | C | H | N |
| Calculated | 86.06 | 7.67 | 6.27 |
| Found | 86.18 | 7.53 | 6.29 |

EXAMPLE 22

Preparation of 1-(4-t-butylphenyl)-3-(4-pyridyl)propane

In a flask, 5.6 g (41.9 mmol) of anhydrous aluminum chloride and 6 ml of dried nitromethane were placed and the mixture was cooled on ice salt bath. A solution of 3.5 g (17.8 mmol) of 1-phenyl-3-(4-pyridyl)-propane dissolved in nitromethane was added thereto, stirred for 30 minutes and a solution of 4.2 g (19.1 mmol) of 2,6-di-t-butyl-p-cresol dissolved in nitromethane was added dropwise. After stirring for one hour at not higher than 0° C., the ice bath was removed and stirred for one hour at room temperature. After completion of the reaction, water was added and the mixture was extracted with ethyl acetate. After drying over anhydrous sodium sulfate, the solvent was distilled away under reduced pressure and the resulting oily substance was purified by silica gel column chromatography to obtain 3.85 g of the desired compound (yield: 85.7%).

The resulting compound was identified as 1-(4-t-butylphenyl)-3-(4-pyridyl)-propane (hereinafter referred to as compound 24).

Oily substance at room temperature
IR(cm$^{-1}$):2870-3080, 1605, 1520
NMR(CDCl$_3$)$\delta$ (ppm):1.28, 9H, s; 1.7-2.15, 2H, m; 2.3-2.7, 4H, m; 6.90, 2H, dd; 6.97, 2H, d; 7.21, 2H, d; 8.33, 2H, dd

| Elementary Analysis (%) | | | |
|---|---|---|---|
| | C | H | N |
| Calculated | 85.32 | 9.15 | 5.53 |
| Found | 85.44 | 9.04 | 5.52 |

EXAMPLE 23

Preparation of 1-phenyl-3-(4-pyridyl)-3-methylbutane

In a flask, 0.63 g (16.5 mmol) of lithium aluminum hydride and 50 ml of dried tetrahydrofuran were placed. During cooling with ice water under a nitrogen atmosphere, a solution of 8.0 g (66.1 mmol) of 4-isopropylpyridine dissolved in tetrahydrofuran was added dropwise. After stirring for 24 hours at room temperature, a solution of 3.05 g of (16.5 mmol) phenetyl bromide dissolved in tetrahydrofuran was added and stirred for 2 hours. After adding water and distilling away tetrahydrofuran under reduced pressure, the residue was extracted with ethyl acetate. After drying over anhydrous sodium sulfate, ethyl acetate was distilled away and the resulting oily substance was purified by silica gel column chromatography to obtain 1.49 g of the desired compound (yield: 10.0%).

The resulting compound was identified as 1-phenyl-3-(4-pyridyl)-3-methylbutane (hereinafter referred to as compound 25) by the following analytical results.

Oily substance at room temperature
IR(cm$^{-1}$):2900-3100, 1610, 1508
NMR(CDCl$_3$)$\delta$ (ppm):1.35, 6H, s; 1.75-2.1, 2H, m; 2.15-2.5, 2H, m; 6.95-7.35, 7H, m; 8.53, 2H, dd

| Elementary Analysis (%) | | | |
|---|---|---|---|
| | C | H | N |
| Calculated | 85.29 | 8.50 | 6.22 |
| Found | 85.50 | 8.30 | 6.20 |

EXAMPLE 24

The following compounds were obtained in the same manner as in Example 1.

(1) 1-(2-chlorophenyl)-3-(4-pyridyl)-propane (hereinafter referred to as compound 26).

Oily substance at room temperature
IR(cm$^{-1}$):2880-3100, 1614, 1483
NMR(CDCl$_3$)$\delta$ (ppm):1.6-2.2, 2H, m; 2.35-2.9, 4H, m; 6.8-7.35, 6H, m; 8.35, 2H, dd

| Elementary Analysis (%) | | | | |
|---|---|---|---|---|
| | C | H | Cl | N |
| Calculated | 72.57 | 6.09 | 15.30 | 6.04 |
| Found | 73.05 | 5.52 | 15.36 | 6.08 |

(2) 1-(4-chlorophenyl)-3-(4-pyridyl)-propane (hereinafter referred to as compound 27).

Oily substance at room temperature
IR(cm$^{-1}$):2880-3100, 1610, 1500
NMR(CDCl$_3$) (ppm):1.7-2.15, 2H, m; 2.5-2.8, 4H, m; 6.95-7.4, 6H, m; 8.48, 2H, dd

| Elementary Analysis (%) | | | | |
|---|---|---|---|---|
| | C | H | Cl | N |
| Calculated | 72.52 | 6.09 | 15.30 | 6.04 |
| Found | 72.04 | 6.51 | 15.37 | 6.08 |

(3) 1-(3,4-dichlorophenyl)-3-(4-pyridyl)-propane (hereinafter referred to as compound 28)

Oily substance at room temperature
IR(cm$^{-1}$):2890-3100, 1614, 1505
NMR(CDCl$_3$)$\delta$ (ppm):1.7-2.2, 2H, m; 2.45-2.9, 4H, m; 6.9-7.45, 6H, m; 8.48, 2H, dd

| Elementary Analysis (%) | | | | |
|---|---|---|---|---|
| | C | H | Cl | N |
| Calculated | 63.18 | 4.92 | 26.64 | 5.26 |
| Found | 63.54 | 4.42 | 26.74 | 5.30 |

(4) 1-phenyl-3-(4-pyridyl)-butane (hereinafter referred to as compound 29)

Oily substance at room temperature
IR(cm$^{-1}$):2890-3100; 1615, 1510
NMR(CDCl$_3$)$\delta$ (ppm):1.24, 3H, d; 1.65-2.15, 2H, m; 2.3-3.0, 3H, m; 6.95-7.4, 7H, m; 8.55, 2H, dd

| Elementary Analysis (%) | | | |
|---|---|---|---|
| | C | H | N |
| Calculated | 85.26 | 8.11 | 6.63 |
| Found | 85.63 | 7.75 | 6.62 |

(5) 1-(3-chlorophenyl)-3-(4-pyridyl)-propane (hereinafter referred to as compound 30)

Oily substance at room temperature
IR(cm$^{-1}$):2860–3080, 1602, 1500
NMR(CDCl$_3$)δ (ppm):1.7–2.2, 2H, m; 2.35–2.8, 4H, m; 6.8–7.2, 6H, m; 8.42, 2H, dd

| Elementary Analysis (%) | | | | |
|---|---|---|---|---|
| | C | H | Cl | N |
| Calculated | 72.57 | 6.09 | 15.30 | 6.04 |
| Found | 72.75 | 5.78 | 15.38 | 6.09 |

(6) 1-(4-methoxyphenyl)-3-(4-pyridyl)-butane (hereinafter referred to as compound 31)

Oily substance at room temperature
IR(cm$^{-1}$):2850–3100, 1608, 1521
NMR(CDCl$_3$)δ (ppm):1.20, 3H, d; 1.6–2.1, 2H, m; 2.2–2.85, 3H, m; 3.65, 3H, s; 6.66, 2H, d; 6.90, 2H, d; 6.93, 2H, dd; 8.36, 2H, dd

| Elementary Analysis (%) | | | |
|---|---|---|---|
| | C | H | N |
| Calculated | 79.63 | 7.94 | 5.80 |
| Found | 79.77 | 7.74 | 5.78 |

(7) 2-phenyl-4-(4-pyridyl)-butane (hereinafter referred to as compound 32)

Oily substance at room temperature
IR(cm$^{-1}$):2900–3100, 1612, 1507
NMR(CDCl$_3$)δ (ppm):1.25, 3H, d; 1.65–2.1, 2H, m; 2.2–2.9, 3H, m; 7.89, 2H, dd; 7.0–7.35, 5H, m; 8.30, 2H, dd

| Elementary Analysis (%) | | | |
|---|---|---|---|
| | C | H | N |
| Calculated | 85.26 | 8.11 | 6.63 |
| Found | 85.15 | 8.25 | 6.61 |

(8) 2-phenyl-4-(4-pyridyl)-pentane (hereinafter referred to as compound 33)

Oily substance at room temperature
IR(cm$^{-1}$):2900–3100, 1616, 1512
NMR(CDCl$_3$)δ (ppm):1.16, 3H, d; 1.22, 3H, d; 1.65–2.05, 2H, m; 2.2–2.9, 2H, m; 6.85–7.3, 7H, m; 8.37, 2H, dd

| Elementary Analysis (%) | | | |
|---|---|---|---|
| | C | H | N |
| Calculated | 85.29 | 8.50 | 6.22 |
| Found | 84.70 | 9.07 | 6.23 |

EXAMPLE 25

The following compounds were obtained in the same manner as in Example 18.

(1) 1-phenyl-3-(3-n-butyl-4-pyridyl)-butane (hereinafter referred to as compound 34)

Oily substance at room temperature
IR(cm$^{-1}$):2890–3110, 1602, 1505
NMR(CDCl$_3$)δ (ppm):0.90, 3H, t; 1.23, 3H, d; 1.1–1.6, 4H, m; 1.7–2.1, 2H, m; 2.35–2.7, 4H, m; 2.8–3.15, 1H, m; 7.0–7.4, 6H, m; 8.33, 1H, s; 8.38, 1H, d

| Elementary Analysis (%) | | | |
|---|---|---|---|
| | C | H | N |
| Calculated | 85.34 | 9.42 | 5.24 |
| Found | 84.66 | 10.12 | 5.22 |

(2) 1-phenyl-3-(3-isobutyl-4-pyridyl)-butane (hereinafter referred to as compound 35)

Oily substance at room temperature
IR(cm$^{-1}$):2880–3110, 1600, 1504
NMR(CDCl$_3$)δ (ppm):0.84, 6H, d; 1.23, 3H, d; 1.4–2.05, 3H, m; 2.2–3.1, 5H, m; 6.9–7.5, 6H, m; 8.28, 1H, s; 8.39, 1H, d

| Elementary Analysis (%) | | | |
|---|---|---|---|
| | C | H | N |
| Calculated | 85.34 | 9.42 | 5.24 |
| Found | 85.37 | 9.39 | 5.24 |

(3) 1-phenyl-3-(3-n-hexyl-4-pyridyl)-butane (hereinafter referred to as compound 36)

Oily substance at room temperature
IR(cm$^{-1}$):2890–3110, 1602, 1508
NMR(CDCl$_3$)δ (ppm):0.89, 3H, t; 1.25, 3H, d; 1.0–1.6, 8H, m; 1.75–2.05, 2H, m; 2.3–2.7, 4H, m; 2.8–3.1, 1H, m; 7.0–7.4, 6H, m; 8.33, 1H, s; 8.37, 1H, d

| Elementary Analysis (%) | | | |
|---|---|---|---|
| | C | H | N |
| Calculated | 85.37 | 9.89 | 4.74 |
| Found | 85.15 | 10.15 | 4.72 |

(4) 1-phenyl-3-(4-pyridyl)-pentane (hereinafter referred to as compound 37)

Oily substance at room temperature
IR(cm$^{-1}$):2890–3100, 1602, 1502
NMR(CDCl$_3$)δ (ppm):0.73, 3H, t; 1.2–2.7, 7H, m; 6.7–7.4, 7H, m; 8.42, 2H, dd

| Elementary Analysis (%) | | | |
|---|---|---|---|
| | C | H | N |
| Calculated | 85.29 | 8.50 | 6.22 |
| Found | 85.20 | 8.62 | 6.18 |

(5) 1-phenyl-3-(4-pyridyl)-4-methylpentane (hereinafter referred to as compound 38)

Oily substance at room temperature
IR(cm$^{-1}$):2870–3070, 1598, 1498
NMR(CDCl$_3$)δ (ppm):0.68, 3H, d; 0.88, 3H, d; 1.5–2.6, 6H, m; 6.8–7.3, 7H, m; 8.39. 2H, dd

| Elementary Analysis (%) | | | |
|---|---|---|---|
| | C | H | N |
| Calculated | 85.31 | 8.84 | 5.83 |
| Found | 85.22 | 9.05 | 5.73 |

EXAMPLE 26

Preparation of 1-(2-fluorophenyl)-4-(4-pyridyl) butane

In a 200-ml flask, 1.53 g (15.1 mmol) of diisopropylamine and 15 ml of tetrahydrofuran were placed and cooled to −50° C. Then, 10.4 ml (16.6 mmol) of n-butyl lithium (15% n-hexane solution) was added thereto under a nitrogen atmosphere. After the resulting mixture was stirred for 10 minutes, a solution of 1.4 g (15.1 mmol) of 4 methylpyridine dissolved in tetrahydrofuran was added dropwise. After stirring for 30 minutes at −50° C., the reaction temperature was gradually raised up to −10° C., which was kept for 30 minutes, and lowered again to −50° C. A solution of 3.3 g (15.1 mmol) of 1-bromo-3-(2-fluorophenyl)-propane dissolved in tetrahydrofuran was added dropwise to the reaction mixture, and after stirring for 30 minutes at −50° C., the temperature was returned to room temperature.

Subsequently, water was added, tetrahydrofuran was distilled away under reduced pressure, the residue was extracted with ethyl acetate, washed with saturated brine and dried over anhydrous sodium sulfate. The solvent was distilled away under reduced pressure and the resulting oily substance was purified by silica gel column chromatography to obtain 2.29 g of the desired compound (yield: 65.9%).

The resulting compound was identified as 1-(2-fluorophenyl)-4-(4-pyridyl)-butane (hereinafter referred to as compound 39) by the following analytical results.

Oily substance at room temperature
NMR(CDCl$_3$)δ (ppm):1.5–1.9, 4H, m; 2.45–2.9, 4H, m; 6.7–7.35, 6H, m; 8.38, 2H, dd

| | Elementary Analysis (%) | | | |
|---|---|---|---|---|
| | C | H | F | N |
| Calculated | 78.57 | 7.03 | 8.29 | 6.11 |
| Found | 78.96 | 6.82 | 8.19 | 6.03 |

EXAMPLE 27

Preparation of 1-(2-fluorophenyl)-4-(4-pyridyl)-pentane 1.62 g (15.1 mmol) of 4-ethylpyridine and 3.3 g (15.1 mmol) of 1-bromo-3-(2-fluorophenyl)-propane were reacted in the same manner as in Example 26. The reaction product was purified to obtain 2.64 g of the desired compound (yield: 71.6%). The resulting compound was identified as 1-(2-fluorophenyl)-4-(4-pyridyl)-pentane (hereinafter referred to as compound 40) by the following analytical results.

Oily substance at room temperature
IR(cm$^{-1}$):2870–3080, 1601, 1496
NMR(CDCl$_3$)δ (ppm):1.20, 3H, d; 1.3–1.8, 4H, m; 2.7–2.9, 3H, m; 6.6–7.4, 6H, m; 8.41, 2H, dd

| | Elementary Analysis (%) | | | |
|---|---|---|---|---|
| | C | H | F | N |
| Calculated | 78.98 | 7.46 | 7.81 | 5.76 |
| Found | 79.24 | 7.42 | 7.68 | 5.67 |

EXAMPLE 28

Preparation of 1-phenyl-4-(3-methyl-4-pyridyl)-butane 1.62 g (15.1 mmol) of 3,4-dimethylpyridine and 3.0 g (15.1 mmol) of 1-bromo-3-phenylpropane were reacted in the same manner as in Example 26. The reaction product was purified to obtain 3.3 g of the desired compound (yield: 97.2%). The resulting compound was identified as 1-phenyl-4-(3-methyl-4-pyridyl)-butane (hereinafter referred to as compound 41) by the following analytical results.

Oily substance at room temperature
IR(cm$^{-1}$):2870–3080, 1600, 1500
NMR(CDCl$_3$)δ (ppm):1.4–1.9, 4H, m; 2.22, 3H, s; 2.4–2.8, 4H, m; 6.97, 1H, d; 7.1–7.4, 5H, m; 8.29, 1H, d; 8.30, 1H, s

| | Elementary Analysis (%) | | |
|---|---|---|---|
| | C | H | N |
| Calculated | 85.29 | 8.50 | 6.22 |
| Found | 85.45 | 8.44 | 6.11 |

EXAMPLE 29

Preparation of 1-phenyl-4-(3-ethyl-4-pyridyl)-butane 1.83 g (15.1 mmol) of 3-ethyl-4-methylpyridine and 3.0 g (15.1 mmol) of 1-bromo-3-phenylpropane were reacted in the same manner as in Example 26. The reaction product was purified to obtain 3.17 g of the desired compound (yield: 87.8%).

The resulting compound was identified as 1-phenyl-4-(3-ethyl-4-pyridyl)-butane (hereinafter referred to as compound 42) by the following analytical results.

Oily substance at room temperature
IR(cm$^{-1}$):2860–3090, 1592, 1495
NMR(CDCl$_3$)δ (ppm):1.19, 3H, t; 1.45–2.0, 4H, m; 2.4–2.95, 6H, m; 6.99, 1H, d; 7.05–7.5, 5H, m; 8.30, 1H, d; 8.34, 1H, s

| | Elementary Analysis (%) | | |
|---|---|---|---|
| | C | H | N |
| Calculated | 85.31 | 8.84 | 5.85 |
| Found | 85.22 | 9.05 | 5.73 |

EXAMPLE 30

Preparation of 1-phenyl 4-(3-methyl-4-pyridyl)-pentane 1.83 g (15.1 mmol) of 3-methyl 4-ethylpyridine and 3.0 g (15.1 mmol) of 1-bromo-3-phenylpropane were reacted in the same manner as in Example 26. The reaction product was purified to obtain 1.40 g of the desired compound (yield: 38.8%).

The resulting compound was identified as b 1-phenyl-4-(3-methyl-4-pyridyl)-pentane (hereinafter referred to as compound 43) by the following analytical results.

Oily substance at room temperature
IR(cm$^{-1}$):2860–3090, 1590, 1495
NMR(CDCl$_3$)δ (ppm):1.16, 3H, d; 1.35–1.8, 4H, m; 2.23, 3H, s; 2.35–3.1, 3H, m; 6.95–7.4, 6H, m; 8.31, 1H, s; 8.34, 1H, d

| | Elementary Analysis (%) | | |
|---|---|---|---|
| | C | H | N |
| Calculated | 85.31 | 8.84 | 5.85 |
| Found | 85.07 | 9.12 | 5.80 |

EXAMPLE 31

Preparation of
1-(2-chlorophenyl)-4-(3-ethyl-4-pyridyl)-butane 1.83 g (15.1 mmol) of 3-ethyl-4-methylpyridine and 3.53 g (15.1 mmol) of 1-bromo-3-(2-chlorophenyl)-propane were reacted in the same manner as in Example 26. The reaction product was purified to obtain 1.62 g of the desired compound (yield: 39.1%).

The resulting compound was identified as 1(-2-chlorophenyl)-4-(3-ethyl-4-pyridyl)-butane (hereinafter referred to as compound 44) by the following analytical results.

Only substance at room temperature
IR(cm$^{-1}$):2890–3080, 1607, 1485
NMR(CDCl$_3$)$\delta$ (ppm):1.21, 3H, t; 1.45–1.9, 4H, m; 2.4–3.0, 6H, m; 6.9–7.55, 5H, m; 8.32, 1H, d; 8.35, 1H, s

| | Elementary Analysis (%) | | | |
|---|---|---|---|---|
| | C | H | Cl | N |
| Calculated | 74.57 | 7.36 | 12.95 | 5.12 |
| Found | 74.69 | 7.57 | 12.73 | 5.02 |

EXAMPLE 32

Preparation of
1-(3-chlorophenyl)-4-(3-ethyl-4-pyridyl)butane 1.83 g (15.1 mmol) of 3-ethyl-4-methylpyridine and 3.53 g (15.1 mmol) of 1-bromo-3-(3-chlorophenyl)-propane were reacted in the same manner as in Example 26. The reaction product was purified to obtain 2.52 g of the desired compound (yield: 61.0%).

The resulting compound was identified as 1-(3-chlorophenyl)-4-(3-ethyl-4-pyridyl)-butane (hereinafter referred to as compound 45) by the following analytical results.

Oily substance at room temperature
IR(cm$^{-1}$):2870–3060, 1597, 1480
NMR(CDCl$_3$)$\delta$ (ppm):1.20, 3H, t; 1.35–1.9, 4H, m; 2.3–2.9, 6H, m; 6.9–7.25, 5H, m; 8.32, 1H, d; 8.35, 1H, s

| | Elementary Analysis (%) | | | |
|---|---|---|---|---|
| | C | H | Cl | N |
| Calculated | 74.57 | 7.36 | 12.95 | 5.12 |
| Found | 74.22 | 7.80 | 12.88 | 5.11 |

EXAMPLE 33

Preparation of
1-(4-chlorophenyl)-4-(3-ethyl-4-pyridyl)butane 1.83 g (15.1 mmol) of 3-ethyl-4-methylpyridine and 3.53 g (15.1 mmol) of 1-bromo-3-(4-chlorophenyl)-propane were reacted in the same manner as in Example 26. The reaction product was purified to obtain 2.33 g of the desired compound (yield: 56.3%).

The resulting compound was identified as 1-(4-chlorophenyl)-4-(3-ethyl-4-pyridyl)-butane (hereinafter referred to as compound 46) by the following analytical results.

Oily substance at room temperature
IR(cm$^{-1}$):2880–3040, 1600, 1498
NMR(CDCl$_3$)$\delta$ (ppm):1.20, 3H, t; 1.35–1.9, 4H, m; 2.2–2.9, 6H, m; 6.99, 1H, d; 7.06, 2H, d; 7.23, 2H, d; 8.31, 1H, d; 8.35, 1H, s

| | Elementary Analysis (%) | | | |
|---|---|---|---|---|
| | C | H | Cl | N |
| Calculated | 74.57 | 7.36 | 12.95 | 5.12 |
| Found | 74.44 | 7.57 | 12.92 | 5.08 |

EXAMPLE 34

Preparation of 1-phenyl-4-(4-pyridyl)-pentane 1.0 g (9.35 mmol) of 4-ethylpyridine and 1.86 g (9.35 mmol) of 1-bromo-3-phenylpropane were reacted in the same manner as in Example 26. The reaction product was purified to obtain 1.17 g of the desired compound (yield: 55.5%).

The resulting compound was identified as 1-phenyl-4-(4-pyridyl)-pentane (hereinafter referred to as compound 47) by the following analytical results.

Oily substance at room temperature
IR(cm$^{-1}$):2870–3090, 1605, 1503
NMR(CDCl$_3$)$\delta$ (ppm):1.20, 3H, d; 1.3–1.8, 4H, m; 2.2–2.9, 3H, m; 6.9–7.5, 7H, m; 8.48, 2H, dd

| | Elementary Analysis (%) | | |
|---|---|---|---|
| | C | H | N |
| Calculated | 85.29 | 8.50 | 6.22 |
| Found | 85.59 | 8.11 | 6.30 |

EXAMPLE 35

Preparation of
1-(3-chlorophenyl)-4-(3-methyl-4-pyridyl) butane 1.0 g (9.35 mmol) of 3,4-dimethylpyridine and 2.18 g (9.35 mmol) of 1-bromo-3-(3-chlorophenyl)-propane were reacted in the same manner as in Example 26. The reaction product was purified to obtain 1.11 g of the desired compound (yield: 5.9%).

The resulting compound was identified as 1-(3-chlorophenyl)-4-(3-methyl-4-pyridyl)-butane (hereinafter referred to as compound 48) by the following analytical results.

Oily substance at room temperature
IR(cm$^{-1}$):2880–3080, 1605, 1483
NMR(CDCl$_3$)$\delta$ (ppm):1.45–1.9, 4H, m, 2.23, 3H, s; 2.4–2.8, 4H. m; 6.9–7.2, 5H, m; 8.2–8.4, 2H, m

| | Elementary Analysis (%) | | | |
|---|---|---|---|---|
| | C | H | Cl | N |
| Calculated | 73.98 | 6.98 | 13.65 | 5.39 |
| Found | 73.90 | 6.92 | 13.75 | 5.43 |

EXAMPLE 36

Preparation of
1-(3-trifluoromethylphenyl)-4-(3-ethyl-4-pyridyl)-butane 1.83 g (15.1 mmol) of 3-ethyl-4-methylpyridine and 4.03 g (15.1 mmol) of 1-bromo-3-(3-trifluoromethylphenyl) propane were reacted in the same manner as in Example 26. The reaction compound was purified to obtain 3.73 g of the desired compound (yield: 80.5%).

The resulting compound was identified as 1-(3-trifluoromethylphenyl)-4-(3-ethyl-4-pyridyl)-butane (hereinafter referred to as compound 49) by the following analytical results.

Oily substance at room temperature
IR(cm$^{-1}$):2890–3080, 1605, 1503
NMR(CDCl$_3$)δ (ppm):1.21, 3H, t; 1.4–1.95, 4H, m; 2.3–3.0, 6H, m; 7.01, 1H, d; 7.2–7.6, 4H, m; 8.31, 1H, d; 8.35, 1H, s

| | Elementary Analysis (%) | | | |
|---|---|---|---|---|
| | C | H | F | N |
| Calculated | 70.34 | 6.56 | 18.54 | 4.56 |
| Found | 70.30 | 7.05 | 18.16 | 4.49 |

EXAMPLE 37

Preparation of 1-(3-trifluoromethylphenyl)-4-(3-methyl-4-pyridyl)-pentane 1.83 g (15.1 mmol) of 3-methyl-4-ethylpyridine and 4.03 g (15.1 mmol) of 1-bromo-3-(3-trifluoromethylphenyl)-propane were reacted in the same manner as in Example 26. The reaction product was purified to obtain 2.20 g of the desired compound (yield: 47.5%).

The resulting compound was identified as 1-(3-trifluoromethylphenyl)-4-(3-methyl-4-pyridyl)-pentane (hereinafter referred to as compound 50) by the following analytical results.

Oily substance at room temperature
IR(cm$^{-1}$):2880–3090, 1605, 1502
NMR(CDCl$_3$)δ (ppm):1.19, 3H, d; 1.4–1.9, 4H, m; 2.26, 3H, s; 2.4–3.2, 3H, m; 7.03, 1H, d; 7.15–7.6, 4H, m;8.33, 1H, s;8.36, 1H, d

| | Elementary Analysis (%) | | | |
|---|---|---|---|---|
| | C | H | F | N |
| Calculated | 70.34 | 6.56 | 18.54 | 4.56 |
| Found | 70.18 | 6.68 | 18.58 | 4.56 |

EXAMPLE 38

Preparation of 1-(3,4-dichlorophenyl)-4-(3-ethyl-4-pyridyl)-butane 1.83 g (15.1 mmol) of 3-ethyl-4-methypyridine and 4.05 g (15.1 mmol) of 1-bromo-3-(3,4-dichlorophenyl)-propane were reacted in the same manner as in Example 26. The reaction product was purified to obtain 2.18 g of the desired compound (yield: 46.9%). The resulting compound was identified as 1-(3,4-dichlorophenyl)-4-(3-ethyl-4-pyridyl)-butane (hereinafter referred to as compound 51) by the following analytical results.

Oily substance at room temperature
IR(cm$^{-1}$):2880–3070, 1600, 1478
NMR(CDCl$_3$)δ (ppm):1.21, 3H, t; 1.4–2.0, 4H, m; 2.3–3.0, 6H, m; 6.8–7.4, 4H, m; 8.32, 1H, d; 8.35, 1H, s

| | Elementary Analysis (%) | | | |
|---|---|---|---|---|
| | C | H | Cl | N |
| Calculated | 66.24 | 6.21 | 23.00 | 4.54 |
| Found | 66.47 | 6.40 | 22.66 | 4.47 |

EXAMPLE 39

Preparation of 1-(3,4-dichlorophenyl)-4-(3-methyl-4-pyridyl)-pentane 1.83 g (15.1 mmol) of 3-methyl-4-ethylpyridine and 4.05 g (15.1 mmol) of 1-bromo-3-(3,4-dichlorophenyl)-propane were reacted in the same manner as in Example 26. The reaction product was purified to obtain 1.73 g of the desired compound (yield:37.3%).

The resulting compound was identified as 1-(3,4-dichlorophenyl)-4-(3-methyl-4-pyridyl)-pentane (hereinafter referred to as compound 52) by the following analytical results.

Oily substance at room temperature
IR(cm$^{-1}$):2880–3070, 1600, 1480
NMR(CDCl$_3$)δ (ppm):1.17, 3H, d; 1.4–1.9, 4H, m; 2.27, 3H, s; 2.35–3.1, 3H, m; 6.85–7.45, 4H, m; 8.33, 1H, s; 8.36, 1H, d

| | Elemental Anaylsis (%) | | | |
|---|---|---|---|---|
| | C | H | Cl | N |
| Calculated | 66.24 | 6.21 | 23.00 | 4.54 |
| Found | 65.97 | 6.58 | 22.92 | 4.54 |

EXAMPLE 40

Preparation of 1-(4-t-butylphenyl)-4-(3-ethyl-4-pyridyl-pentane

In a flask, 1.9g (14.2 mmol) of anhydrous aluminum chloride and 2 ml of dried nitromethane were placed and cooled on an ice bath including salt. A solution of 1.5 g (6.3 mmol) of 1-phenyl-4-(3-ethyl-4-pyridyl)-butane dissolved in nitromethane was added thereto and the mixture was stirred for 30 minutes and a solution of 1.4 g (6.4 mmol) of 2,6-dit-tutyl-p-cresol dissolved in nitromethane was added dropwise. After the resulting mixture was stirred for one hour at not more than 0° C., the ice bath was removed and stirred for one hour at room temperature. After the reaction was over, water was added and the mixture was extracted with ethyl acetate. After drying over anhydrous sodium sulfate, the solvent was distilled away under reduced pressure and the resulting oily substance was purified by silica gel column chromatography to obtain 1.2 g of the desired compound (yield: 62.6%).

The resulting compound was identified as 1-(4-t-butylphenyl)-4-(3-ethyl-4-pyridyl)-butane (hereinafter referred to as compound 53) by the following analytical results.

Oily substance at room temperature
IR(cm$^{-1}$):2880–3080, 1605, 1522
NMR(CDCl$_3$)δ (ppm):1.19, 3H, t; 1.31, 9H, s; 1.5–1.9, 4H, m; 2.45–2.8, 6H, m; 7.01, 1H, d; 7.09, 2H, d; 7.31, 2H, d; 8.31, 1H, d; 8.34, 1H, s

| | Elementary Analysis (%) | | |
|---|---|---|---|
| | C | H | N |
| Calculated | 85.37 | 9.89 | 4.74 |
| Found | 85.32 | 10.02 | 4.66 |

EXAMPLE 41

Preparation of
1-phenyl-4-(3-ethyl-4-pyridyl)-1,3-butadiene

In a 200-ml flask, 0.94 g (9.35 mmol) of diisopropylamine and 15 ml of tetrahydrofuran were placed and cooled to −50° C. Then, 6.5 ml (10.3 mmol) of n-butyl lithium (15% n-hexane solution) was added thereto under a nitrogen atmosphere. The resulting mixture was stirred for 10 minutes, and a solution of 1.13 g (9.35 mmol) of 3-ethyl-4-methylpyridine dissolved in tetrahydrofuran was added dropwise. After stirring for 30 minutes at −50° C., the reaction temperature was gradually raised up to −10° C., which was kept for 30 minutes, and lowered again to −50° C. A solution of 1.23 g (9.35 mmol) of cinnamic aldehyde dissolved in tetrahydrofuran was added dropwise to the reaction mixture, and after stirring for 30 minutes at −50° C., the temperature was returned to room temperature. Subsequently, water was added, tetrahydrofuran was distilled away under reduced pressure, and the residue was extracted with ethyl acetate. The extract was washed with saturated brine, then dried over anhydrous sodium sulfate. Then, the solvent was distilled away under reduced pressure, to obtain 2.34 g (Yield: 99.1%) of an oily substance.

To the alcoholic substance thus obtained, 4 ml of 65% sulfuric acid was added and heated for 2 hours at 100° C. After cooling, water was added. The resulting mixture was made basic with sodium carbonate and then extracted with ethyl acetate. Subsequently, after the ethyl acetate layer was dried over anhydrous sodium sulfate, the solvent was distilled away under reduced pressure, and then the resulting oily substance was purified by silica gel column chromatography, to obtain 0.28 g (yield: 12.7%) of the desired compound.

The resulting compound was identified as (E, E)-1-phenyl-4-(3-ethyl-4-pyridyl)-1,3-butadiene (hereinafter referred to as compound 54) by infrared ray absorption spectrum (IR), nuclear magnetic resonance spectrum (NMR) and elementary analysis.

Melting Point 75.0°–76.2° C.
IR(cm$^{-1}$):2900–3060, 1600, 1500
NMR(CDCl$_3$)δ (ppm):1.24, 3H, t; 2.73, 3H, q; 6.6–7.6, 10H, m; 8.39, 1H, d; 8.39, 1H, s

| | Elementary Analysis (%) | | |
|---|---|---|---|
| | C | H | N |
| Calculated | 86.77 | 7.28 | 5.95 |
| Found | 87.00 | 6.95 | 6.04 |

EXAMPLE 42

The procedure of Example 41 was repeated with the exception that 3.5 g of benzyl acetone in place of cinnamic aldehyde and 2.26 g of 3-ethyl-4-methylpyridine were used in Example 41, to obtain 3.26 g (yield: 59.8%) of (E)-1-(3-ethyl-4-pyridyl)-2-methyl-4-phenyl -1-butene (hereinafter referred to as compound 55) and o.95 g (yield: 17.4%) of (Z)-1-(3-ethyl-4-pyridyl)-2-methyl-4-phenyl-1-butene (hereinafter referred to as compound 56). The analytical results are shown below.
compound 55
IR(cm$^{-1}$):2900–3120, 1602, 1507
NMR(CDCl$_3$)δ (ppm):1.08, 3H, t; 1.74, 3H, d; 2.3–3.0, 6H, m; 6.15, 1H, br s; 6.97, 1H, d; 7.1–7.5, 5H, m; 8.34, 1H, d; 8.36, 1H, s

| | Elementary Analysis (%) | | |
|---|---|---|---|
| | C | H | N |
| Calculated | 86.01 | 8.42 | 5.57 |
| Found | 86.22 | 8.35 | 5.42 | compound 56
IR(cm$^{-1}$):2890–3110, 1598, 1501
NMR(CDCl$_3$)δ (ppm) 1.12, 3H, t; 1.98, 3H, d; 2.2–2.9, 6H, m; 6.22, 1H, br s; 6.78, 1H, d; 6.9–7.4, 5H, m; 8.30, 1H, d; 8.36, 1H, s

| | Elementary Analysis (%) | | |
|---|---|---|---|
| | C | H | N |
| Calculated | 86.01 | 8.42 | 5.57 |
| Found | 86.03 | 8.25 | 5.70 |

EXAMPLE 43

The procedure of Example 41 was repeated with the exception that 3.5 g of benzal acetone in place of cinnamic aldehyde and 2.26 g o±3-ethyl-4-methylpyridine were used in Example 41, to obtain 0.35 g (yield: 7.3%) of (E,E)-1-(3-ethyl-4-pyridyl)-2-methyl-4-phenyl -1,3-butadiene (hereinafter referred to as compound 57) and 0.22 g (yield: 4.7%) of (Z,E)-1-(3-ethyl-4-pyridyl)-2-methyl-4-phenyl-1,3-butadiene (hereinafter referred to as compound 58). The analytical results are shown below.
compound 57
IR(cm$^{-1}$):2900–3060, 1599, 1500
NMR(CDCl$_3$)δ (ppm):1.20, 3H, t; 2.01, 3H, d; 2.66, 2H, q; 6.61, 1H, br s; 6.70, 1H, d; 7.03, 1H, d; 7.11, 1H, d; 7.2–7.6, 5H, m; 8.42, 1H, d; 8.45, 1H, s

| | Elementary Analysis (%) | | |
|---|---|---|---|
| | C | H | N |
| Calculated | 86.71 | 7.68 | 5.61 |
| Found | 86.96 | 7.60 | 5.46 | compound 58
IR(cm$^{-1}$):2890–3040, 1595, 1500
NMR(CDCl$_3$)δ (ppm) 1.20, 3H, t; 2.18, 3H, d; 2.66, 2H, q; 6.47, 1H, br s; 6.72, 1H, d; 7.04, 1H, d; 7.13, 1H, 43, 1H, d; 8.46, 1H, s

| | Elementary Analysis (%) | | |
|---|---|---|---|
| | C | H | N |
| Calculated | 86.71 | 7.68 | 5.61 |
| Found | 86.99 | 7.55 | 5.46 |

EXAMPLE 44

Preparation of 2-methyl-2-(4-pyridyl)-5-phenylhexane

In a flask, 0.61 g (18 mmol) of lithium aluminum hydride and 50 ml of dried tetrahydrofuran were placed. While cooling with ice-cold water under a nitrogen atmosphere, a solution of 10.0 g (82.6 mmol) of 4-isopropylpyridine dissolved in tetrahydrofuran was added dropwise. After stirring for 24 hours at room temperature, a solution of 3.41 g (16.0 mmol) of 4-phenylbutyl bromide dissolved in tetrahydrofuran was added. The resulting mixture was stirred for 2 hours. Subsequently, water was added, tetrahydrofuran was distilled away under reduced pressure, and then the residue was extracted with ethyl acetate. After the extract was dried over anhydrous sodium sulfate, ethyl acetate was distilled away under reduced pressure. The resulting oily substance was purified by silica gel column chromatography, to obtain 0.21 g (yield: 5.2%) of the desired compound.

The resulting compound was identified as 2-methyl-2-(4-pyridyl)-5-phenylhexane (hereinafter referred to as compound 59) by the analytical results shown below.

Oily substance at room temperature
IR(cm$^{-1}$):2900–3110, 1612, 1508
NMR(CDCl$_3$)δ (ppm) 1.15, 3H, d; 1.21, 3H, s; 1.24, 3H, s; 1.3–1.7, 2H, m; 2.54, 1H, q; 6.9–7.4, 7H, m; 8.47, 2H, dd

| | Elementary Analysis (%) | | |
|---|---|---|---|
| | C | H | N |
| Calculated | 85.33 | 9.15 | 5.52 |
| Found | 85.40 | 8.82 | 5.79 |

EXAMPLE 45

The procedure of Example 44 was repeated with the exception that 3.18 g of 3-phenylpropyl bromide was used in place of 4-phenylbutyl bromide in Example 44, to obtain 0.22 g (yield: 5.8%) of 1-phenyl-4-methyl 4-(4-pyridyl)-pentane (hereinafter referred to as compound 60).

Oily substance at room temperature
IR(cm$^{-1}$):2900–3120, 1618, 1515
NMR(CDCl$_3$)δ (ppm) 1.27, 6H, s; 1.3–1.8, 4H, m; 2.52, 2H, t; 7.0–7.35, 7H, m; 8.48, 2H, dd

| | Elementary Analysis (%) | | |
|---|---|---|---|
| | C | H | N |
| Calculated | 85.31 | 8.84 | 5.85 |
| Found | 85.64 | 8.77 | 5.61 |

EXAMPLE 46

The reaction of Example 1 was repeated by using the compounds shown below in the amounts below as the starting materials, to give the compounds 61 to 89 shown below. Compound 61

| Starting materials: | |
|---|---|
| 3,4-diethylpridine | (1.26 g) |
| 1-phenyl-3-bromopropane | (1.86 g) |
| Product: | |
| 1-phenyl-4-(3-ethyl-4-pyridyl)-pentane | (compound 61) |

Oily substance at room temperature
IR(cm$^{-1}$):2870–3070, 1598, 1479
NMR(CDCl$_3$)δ (ppm):1.19, 3H, d; 1.20, 3H, t; 1.35–1.8, 4H, m; 2.4–3.1, 5H, m; 7.04, 1H, d; 7.1–7.4, 5H, m; 8.34, 1H, d; 8.35, 1H, d

| | Elementary Analysis (%) | | |
|---|---|---|---|
| | C | H | N |
| Calculated | 85.33 | 9.15 | 5.52 |
| Found | 84.85 | 8.82 | 5.33 |
| Yield | 52.3% | | |

Compound 62

| Starting materials: | |
|---|---|
| 3-ethyl-4-methylpyridine | (1.13 g) |
| 1-phenyl-2-methyl-3-bromo-1-propene | (1.97 g) |
| Product: | |
| (E)-1-phenyl-2-methyl-4-(3-ethyl-4-pyridyl)-1-butene | (compound 62) |

Oily substance at room temperature
IR(cm$^{-1}$):2900–3080, 1604, 1501
NMR(CDCl$_3$)δ (ppm):1.27, 3H, t; 1.92, 3H, d; 2.3–3.0, 6H, m; 6.26, 1H, br s; 6.9–7.45, 6H, m; 8.36, 1H, d; 8.40, 1H, s

| | Elementary Analysis (%) | | |
|---|---|---|---|
| | C | H | N |
| Calculated | 86.00 | 8.42 | 5.57 |
| Found | 85.71 | 8.45 | 5.84 |
| Yield | 12.8% | | |

Compound 63

| Starting materials: | |
|---|---|
| 3,4-diethylpyridine | (1.26 g) |
| 1-phenyl-2-methyl-3-bromo-1-propene | (1.97 g) |
| Product: | |
| (E)-1-phenyl-2-methyl-4-(3-ethyl-4-pyridiyl)-1-pentene | (compound 63) |

Oily substance at room temperature
IR(cm$^{-1}$):2900–3080, 1607, 1502
NMR(CDCl$_3$)δ (ppm):1.24, 3H, t; 1.25, 3H, d; 1.82, 3H, d; 2.39, 2H, d; 2.70, 2H, q; 3.1–3.4, 1H, m; 6.23, 1H, br s; 7.0–7.45, 6H, m; 8.37, 1H, s; 8.39, 1H, d

| | Elementary Analysis (%) | | |
|---|---|---|---|
| | C | H | N |
| Calculated | 85.98 | 8.74 | 5.28 |
| Found | 85.60 | 8.92 | 5.47 |
| Yield | 16.8% | | |

Compound 64

| Starting materials: | |
|---|---|
| 3-ethyl-4-methylpyridine | (1.13 g) |
| 1-phenyl-2-methyl-3-bromopropane | (2.0 g) |
| Product: | |
| 1-phenyl-2-methyl-4-(3-ethyl-4-pyridyl)-butane | (compound 64) |

Oily substance at room temperature
IR(cm$^{-1}$):2880–3100, 1598, 1500
NMR(CDCl$_3$)δ (ppm):0.97, 3H, d; 1.19, 3H, t; 1.3–2.0, 3H, m; 2.4–2.8, 6H, m; 6.99, 1H, d; 7.0–7.45, 5H, m; 8.30, 1H, d; 8.34, 1H, s

| Elementary Analysis (%) | | | |
|---|---|---|---|
| | C | H | N |
| Calculated | 85.33 | 9.15 | 5.52 |
| Found | 85.22 | 8.95 | 5.82 |
| Yield | 59.2% | | |

Compound 65

| Starting materials: | |
|---|---|
| 3-ethyl-4-methylpyridine | (1.13 g) |
| 1-(2-methylphenyl)-3-bromopropane | (2.0 g) |
| Product: | |
| 1-(2-methylphenyl)-4-(3-ethyl-4-pyridyl)-butane | (compound 65) |

Oily substance at room temperature
IR(cm$^{-1}$):2880–3060, 1598, 1496
NMR(CDCl$_3$)δ (ppm):1.22, 3H, t; 1.5–1.8, 4H, m; 2.30, 3H, s; 2.5–2.8, 6H, m; 7.05, 1H, d; 7.11, 4H, s; 8.33, 1H, d; 8.37, 1H, s

| Elementary Analysis (%) | | | |
|---|---|---|---|
| | C | H | N |
| Calculated | 85.33 | 9.15 | 5.52 |
| Found | 85.08 | 9.14 | 5.79 |
| Yield | 72.0% | | |

Compound 66

| Starting materials: | 3-ethyl-4-methylpyridine (1.13 g) |
|---|---|
| | 1-(3-methyphenyl)-3-bromopropane (2.0 g) |
| Product: | 1-(3-methylphenyl)-4-(3-ethyl-4-pyridyl)-butane (compound 66) |

Oily substance at room temperature
IR(cm$^{-1}$):2890–3050, 1607, 1500
NMR(CDCl$_3$)δ (ppm):1.20, 3H, t; 1.4–1.9, 4H, m; 2.32, 3H, s; 2.4–2.9, 6H, m; 6.75–7.5, 5H, m; 8.31, 1H, d; 8.36, 1H, s

| Elementary Analysis (%) | | | |
|---|---|---|---|
| | C | H | N |
| Calculated | 85.33 | 9.15 | 5.52 |
| Found | 85.44 | 8.79 | 5.77 |
| Yield | 66.5% | | |

Compound 67

| Starting materials: | 3-ethyl-4-methylpyridine (1.13 g) |
|---|---|
| | 1-(4-methylphenyl)-3-bromopropane (2.0 g) |
| Product: | 1-(4-methylphenyl)-4-(3-ethyl-4-pyridyl)-butane (compound 67) |

Oily substance at room temperature
IR(cm$^{-1}$):2900–3080, 1620, 1510
NMR(CDCl$_3$)δ (ppm):1.21, 3H, t; 1.5–1.8, 4H, m; 2.31, 3H, s; 2.5–2.8, 6H, m; 7.04, 1H, d; 7.07, 4H, s; 8.32, 1H, d; 8.35, 1H, s

| Elementary Analysis (%) | | | |
|---|---|---|---|
| | C | H | N |
| Calculated | 85.33 | 9.15 | 5.52 |
| Found | 85.00 | 9.44 | 5.56 |
| Yield | 37.0% | | |

Compound 68

| Starting materials: | 3-ethyl-4-methylpyridine (1.13 g) |
|---|---|
| | 1-(3-chloro-4-methylphenyl)-3-bromopropane (2.31 g) |
| Product: | 1-(3-chloro-4-methylphenyl)-4-(3-ethyl-4-pyridyl)-butane (compound 68) |

Oily substance at room temperature
IR(cm$^{-1}$):2880–3040, 1600, 1500
NMR(CDCl$_3$)δ (ppm):1.20, 3H, t; 1.4–1.8, 4H, m; 2.32, 2H, s; 2.4–2.8, 6H, m; 6.95–7.3, 4H, m; 8.32, 1H, d; 8.35, 1H, s

| Elementary Analysis (%) | | | | |
|---|---|---|---|---|
| | C | H | Cl | N |
| Calculated | 75.12 | 7.70 | 12.32 | 4.86 |
| Found | 74.94 | 7.54 | 12.46 | 5.06 |
| Yield | 53.1% | | | |

Compound 69

| Starting materials: | 3-ethyl-4-methylpyridine (1.13 g) |
|---|---|
| | 1-bromo-3-phenylbutane (2.0 g) |
| Product: | 1-(3-ethyl-4-pyridyl)-4-phenylpentane (compound 69) |

Oily substance at room temperature
IR(cm$^{-1}$):2890–3080, 1600, 1500
NMR(CDCl$_3$)δ (ppm):1.16, 3H, t; 1.24, 3H, d; 1.4–1.8, 4H, m; 2.4–2.9, 5H, m; 6.94, 1H, d; 7.0–7.4, 5H, m; 8.29, 1H, d; 8.32, 1H, s

| Elementary Analysis (%) | | | |
|---|---|---|---|
| | C | H | N |
| Calculated | 85.33 | 9.15 | 5.52 |
| Found | 84.91 | 9.34 | 5.75 |
| Yield | 59.3% | | |

Compound 70

| Starting materials: | 3-methyl-4-ethylpyridine (1.13 g) |
|---|---|
| | 1-bromo-2-methyl-3-phenylbutane (2.12 g) |
| Product: | 2-phenyl-3-methyl-5-(3-methyl-4-pyridyl)-hexane (compound 70) |

Oily substance at room temperature
IR(cm$^{-1}$):2900–3090, 1603, 1504
NMR(CDCl$_3$)δ (ppm):0.80, 3H, d; 1.13, 3H, d; 1.24, 3H, d; 1.4–2.0, 3H, m; 2.25, 3H, s; 2.3–3.2, 2H, m; 6.9–7.4, 6H, m; 8.31, 1H, s; 8.35, 1H, d

| Elementary Analysis (%) | | | |
|---|---|---|---|
| | C | H | N |
| Calculated | 85.34 | 9.43 | 5.23 |
| Found | 85.61 | 9.26 | 5.11 |

-continued

| Elementary Analysis (%) | | | |
|---|---|---|---|
| | C | H | N |
| Yield | 24.8% | | |

Compound 71

| Starting materials: | 4-methylpyridine (0.87 g) |
|---|---|
| | 1-bromo-4-phenylbutane (2.0 g) |
| Product: | 1-phenyl-5-(4-pyridyl)-pentane (compound 71) |

Oily substance at room temperature
IR(cm$^{-1}$):2860–3070, 1606, 1500
NMR(CDCl$_3$)δ (ppm):1.2–1.8, 6H, m; 2.4–2.7, 4H, m; 7.03, 2H, dd; 7.1–7.4, 5H, m; 8.45, 2H, dd

| | Elementary Analysis (%) | | |
|---|---|---|---|
| | C | H | N |
| Calculated | 85.29 | 8.50 | 6.21 |
| Found | 85.58 | 8.22 | 6.27 |
| Yield | 65.7% | | |

Compound 72

| Starting materials: | 4-ethylpyridine (1.0 g) |
|---|---|
| | 1-bromo-4-phenylbutane (2.0 g) |
| Product: | 1-phenyl-5-(4-pyridyl)-hexane (compound 72) |

Oily substance at room temperature
IR(cm$^{-1}$):2860–3080, 1600, 1500
NMR(CDCl$_3$)δ (ppm):1.17, 3H, d; 1.2–1.8, 6H, m; 2.3–2.8, 3H, m; 6.92, 2H, dd; 7.08, 5H, s; 8.35, 2H, dd

| | Elementary Analysis (%) | | |
|---|---|---|---|
| | C | H | N |
| Calculated | 85.31 | 8.84 | 5.85 |
| Found | 85.04 | 9.06 | 5.92 |
| Yield | 89.3% | | |

Compound 73

| Starting materials: | 3,4-dimethylpyridine (1.0 g) |
|---|---|
| | 1-bromo-4-phenylbutane (2.0 g) |
| Product: | 1-phenyl-5-(3-methyl-4-pyridyl)-pentane (compound 73) |

Oily substance at room temperature
IR(cm$^{-1}$):2860–3070, 1600, 1500
NMR(CDCl$_3$)δ (ppm):1.2–1.8, 6H, m; 1.24, 3H, s; 2.4–2.7, 4H, m; 6.99, 1H, d; 7.05–7.4, 5H, m; 8.30, 1H, d; 8.31, 1H, s

| | Elementary Analysis (%) | | |
|---|---|---|---|
| | C | H | N |
| Calculated | 85.31 | 8.84 | 5.85 |
| Found | 85.24 | 9.02 | 5.72 |
| Yield | 25.4% | | |

Compound 74

| Starting materials: | 3-ethyl-4-methylpyridine (1.13 g) |
|---|---|
| | 1-bromo-4-phenylbutane (2.0 g) |
| Product: | 1-phenyl-5-(3-ethyl-4-pyridyl)-pentane (compound 74) |

Oily substance at room temperature
IR(cm$^{-1}$):2880–3080, 1602, 1504
NMR(CDCl$_3$)δ (ppm):1.21, 3H, t; 1.3–1.9, 6H, m; 2.4–2.9, 6H, m; 7.00, 1H, d; 7.05–7.45, 5H, m; 8.32, 1H, d; 8.35, 1H, s

| | Elementary Analysis (%) | | |
|---|---|---|---|
| | C | H | N |
| Calculated | 85.33 | 9.15 | 5.52 |
| Found | 85.01 | 9.39 | 5.60 |
| Yield | 46.2% | | |

Compound 75

| Starting materials: | 3-methyl-4-ethylpyridine (1.13 g) |
|---|---|
| | 1-bromo-4-phenylbutane (2.0 g) |
| Product: | 1-phenyl-5-(3-methyl-4-pyridyl)-hexane (compound 75) |

Oily substance at room temperature
IR(cm$^{-1}$):2860–3070, 1598, 1498
NMR(CDCl$_3$)δ (ppm):1.17, 3H, d; 1.2–1.8, 6H, m; 2.26, 3H, s; 2.57, 2H, t; 2.7–3.1, 1H, m; 7.06, 1H, d; 7.1–7.4, 5H, m; 8.33, 1H, s; 8.36, 1H, d

| | Elementary Analysis (%) | | |
|---|---|---|---|
| | C | H | N |
| Calculated | 85.33 | 9.15 | 5.52 |
| Found | 85.71 | 9.00 | 5.28 |
| Yield | 20.7% | | |

Compound 76

| Starting materials: | 3-ethyl-4-methylpyridine (1.13 g) |
|---|---|
| | 1-bromo-4-(2-chlorophenyl)-butane (2.31 g) |
| Product: | 1-(2-chlorophenyl)-5-(3-ethyl-4-pyridyl)-pentane |

Oily substance at room temperature
IR(cm$^{-1}$):2880–3080, 1602, 1481
NMR(CDCl$_3$)δ (ppm):1.22, 3H, t; 1.35–1.9, 6H, m; 2.45–2.9, 6H, m; 6.9–7.4, 5H, m; 8.32, 1H, m; 8.35, 1H, s

| | Elementary Analysis (%) | | | |
|---|---|---|---|---|
| | C | H | Cl | N |
| Calculated | 75.12 | 7.70 | 12.32 | 4.86 |
| Found | 74.96 | 7.74 | 12.10 | 5.08 |
| Yield | 7.6% | | | |

Compound 77

| Starting materials: | | |
|---|---|---|
| 3-ethyl-4-methylpyridine | (1.13 g) | |
| 1-bromo-4-(3-chlorophenyl)-butane | (2.31 g) | |
| Product: 1-(3-chlorophenyl)-5-(3-ethyl-4-pyridyl)-pentane | (compound 77) | |

Oily substance at room temperature

IR(cm⁻¹):2880–3050, 1601, 1500
NMR(CDCl₃)δ (ppm):1.22, 3H, t; 1.35–1.9, 6H, m; 2.60, 6H, t; 6.9–7.4, 5H, m; 8.32, 1H, d; 8.35, 1H, s

| | Elementary Analysis (%) | | | |
|---|---|---|---|---|
| | C | H | Cl | N |
| Calculated | 75.12 | 7.70 | 12.32 | 4.86 |
| Found | 75.20 | 7.95 | 12.15 | 4.71 |
| Yield | 18.8% | | | |

Compound 78

| Starting materials: | |
|---|---|
| 3-ethyl-4-methylpyridine | (1.13 g) |
| 1-bromo-4-(4-chlorophenyl)-butane | (2.31 g) |
| Product: 1-(4-chlorophenyl)-5-(3-ethyl-4-pyridyl)-pentane | (compound 78) |

Oily substance at room temperature
IR(cm⁻¹):2880–3050, 1602, 1502
NMR(CDCl₃)δ (ppm):1.22, 3H, t; 1.35–1.90, 6H, m; 2.60, 6H, t; 6.9–7.4, 5H, m; 8.32, 1H, d; 8.35, 1H, s

| | Elementary Analysis (%) | | | |
|---|---|---|---|---|
| | C | H | Cl | N |
| Calculated | 75.12 | 7.70 | 12.32 | 4.86 |
| Found | 75.26 | 7.83 | 12.20 | 4.68 |
| Yield | 11.6% | | | |

Compound 79

| Starting materials: | |
|---|---|
| 4-methylpyridine | (0.87 g) |
| 1-bromo-5-phenylpentane | (2.1 g) |
| Product: 1-phenyl-6-(4-pyridyl)-hexane | (compound 79) |

Oily substance at room temperature
IR(cm⁻¹):2870–3090, 1612, 1505
NMR(CDCl₃)δ (ppm):1.2–1.9, 8H, m; 2.4–2.8, 4H, m; 7.03, 2H, dd; 7.1–7.4, 5H, m; 8.45, 2H, dd

| | Elementary Analysis (%) | | |
|---|---|---|---|
| | C | H | N |
| Calculated | 85.31 | 8.84 | 5.85 |
| Found | 85.62 | 8.56 | 5.81 |
| Yield | 80.2% | | |

Compound 80

| Starting materials: | |
|---|---|
| 4-ethylpyridine | (1.0 g) |
| 1-bromo-5-phenylpentane | (2.1 g) |
| Product: 1-phenyl-6-(4-pyridyl)-heptane | (compound 80) |

Oily substance at room temperature
IR(cm⁻¹):2870–3080, 1601, 1501
NMR(CDCl₃)δ (ppm):1.19, 3H, d; 1.3–1.8, 8H, m; 2.4–2.8, 3H, m; 7.04, 2H, dd; 7.1–7.4, 5H, m; 8.47, 2H, dd

| | Elementary Analysis (%) | | |
|---|---|---|---|
| | C | H | N |
| Calculated | 85.33 | 9.15 | 5.52 |
| Found | 85.07 | 9.25 | 5.68 |
| Yield | 79.8% | | |

Compound 81

| Starting materials: | |
|---|---|
| 3-ethyl-4-methylpyridine | (1.13 g) |
| 1-bromo-5-phenylpentane | (2.1 g) |
| Product: 1-phenyl-6-(3-ethyl-4-pyridyl)-hexane | (compound 81) |

Oily substance at room temperature
IR(cm⁻¹):2870–3070, 1601, 1502
NMR(CDCl₃)δ (ppm):1.21, 3H, t; 1.2–1.8, 8H, m; 2.4–2.8, 6H, m; 7.00, 1H, d; 7.05–7.45, 5H, m; 8.31, 1H, d; 8.35, 1H, s

| | Elementary Analysis (%) | | |
|---|---|---|---|
| | C | H | N |
| Calculated | 85.34 | 9.43 | 5.23 |
| Found | 85.75 | 9.26 | 4.98 |
| Yield | 39.9% | | |

Compound 82

| Starting materials: | |
|---|---|
| 3-ethyl-4-methylpyridine | (1.13 g) |
| 1-bromo-6-phenylhexane | (2.25 g) |
| Product: 1-phenyl-7-(3-ethyl-4-pyridyl)-heptane | (compound 82) |

Oily substance at room temperature
IR(cm⁻¹):2880–3080, 1605, 1501
NMR(CDCl₃)δ (ppm):1.22, 3H, t; 1.3–1.8, 10H, m; 2.5–2.8, 6H, m; 7.03, 1H, d; 7.1–7.5, 5H, m; 8.32, 1H, d; 8.35, 1H, s

| | Elementary Analysis (%) | | |
|---|---|---|---|
| | C | H | N |
| Calculated | 85.36 | 9.67 | 4.97 |
| Found | 85.49 | 9.38 | 5.13 |
| Yield | 16.1% | | |

Compound 83

| Starting materials: | |
|---|---|
| 3-ethyl-4-methylpyridine | (1.13 g) |
| 1-bromo-7-phenylheptane | (2.38 g) |
| Product: 1-phenyl-8-(3-ethyl-4-pyridyl)-octane | (compound 83) |

Oily substance at room temperature
IR(cm⁻¹):2850–3060, 1597, 1498
NMR(CDCl₃)δ (ppm):1.21, 3H, t; 1.2–1.8, 12H, m; 2.59, 4H, t; 2.64, 2H, q; 7.02, 1H, d; 7.1–7.4, 5H, m; 8.32, 1H, d; 8.35, 1H, s

| Elementary Analysis (%) | | | |
|---|---|---|---|
| | C | H | N |
| Calculated | 85.37 | 9.89 | 4.74 |
| Found | 85.43 | 9.63 | 4.92 |
| Yield | 44.2% | | |

Compound 84

| Starting materials: | | |
|---|---|---|
| 4-ethylpyridine | | (1.0 g) |
| 1-bromo-7-phenylheptane | | (2.38 g) |
| Product: 1-phenyl-8-(4-pyridyl)-nonane | | (compound 84) |

Oily substance at room temperature
IR(cm$^{-1}$):2860–3080, 1603, 1500
NMR(CDCl$_3$)δ (ppm):1.29, 3H, d; 1.2–1.8, 12H, m; 2.4–2.85, 3H, m; 7.06, 2H, dd; 7.1–7.4, 5H, m; 8.47, 2H, dd

| Elementary analysis (%) | | | |
|---|---|---|---|
| | C | H | N |
| Calculated | 85.36 | 9.67 | 4.97 |
| Found | 85.31 | 9.85 | 4.81 |
| Yield | 42.2% | | |

Compound 85

| Starting materials: | | |
|---|---|---|
| 3-ethyl-4-methylpyridine | | (1.13 g) |
| 1-bromo-2-(2-methylphenyl)-ethane | | (1.86 g) |
| Product: 1-(2-methylphenyl)-3-(3-ethyl-4-pyridyl)-propane | | (compound 85) |

Oily substance at room temperature
IR(cm$^{-1}$):2870–3050, 1597, 1494
NMR(CDCl$_3$)δ (ppm):1.19, 3H, t; 1.8–2.1, 2H, m; 2.26, 3H, s; 2.4–2.9, 6H, m; 6.9–7.3, 5H, m; 8.28, 1H, d; 8.31, 1H, s

| Elementary Analysis (%) | | | |
|---|---|---|---|
| | C | H | N |
| Calculated | 85.31 | 8.84 | 5.85 |
| Found | 85.34 | 8.54 | 6.12 |
| Yield | 63.0% | | |

Compound 86

| Starting materials: | | |
|---|---|---|
| 3-ethyl-4-methylpyridine | | (1.13 g) |
| 1-bromo-2-(3-methylphenyl)-ethane | | (1.86 g) |
| Product: 1-(3-methylphenyl)-3-(3-ethyl-4-pyridyl)-propane | | (compound 86) |

Oily substance at room temperature
IR(cm$^{-1}$):2900–3050, 1605, 1500
NMR(CDCl$_3$)δ (ppm):1.19, 3H, t; 1.7–2.1, 2H, m; 2.33, 3H, s; 2.4–2.8, 6H, m; 6.9–7.3, 5H, m; 8.32, 1H, d; 8.36, 1H, s

| Elementary Analysis (%) | | | |
|---|---|---|---|
| | C | H | N |
| Calculated | 85.31 | 8.84 | 5.85 |
| Found | 85.44 | 8.64 | 5.92 |
| Yield | 35.0% | | |

Compound 87

| Starting materials: | 3-ethyl-4-methylpyridine | (1.13 g) |
|---|---|---|
| | 1-bromo-2-phenylpropane | (1.86 g) |
| Product: | 1-(3-ethyl-4-pyridyl)-3-phenylbutane | (compound 87) |

Oily substance at room temperature
IR(cm$^{-1}$):2880–3070, 1597, 1498
NMR(CDCl$_3$)δ (ppm):1.13, 3H, t; 1.31, 3H, d; 1.7–2.1, 2H, m; 2.3 –2.9, 5H, m; 6.9–7.45, 6H, m; 8.30, 1H, d; 8.32, 1H, s

| Elementary Analysis (%) | | | |
|---|---|---|---|
| | C | H | N |
| Calculated | 85.31 | 8.84 | 5.85 |
| Found | 85.12 | 9.22 | 5.65 |
| Yield | 40.0% | | |

Compound 88

| Starting materials: | 3-ethyl-4-methylpyridine | (1.13 g) |
|---|---|---|
| | 1-bromo-2-(3-chloro-4-methylphenyl)ethane | (2.18 g) |
| Product: | 1-(3-chloro-4-methylphenyl)-3-(3-ethyl-4-pyridyl)-propane | (compound 88) |

Oily substance at room temperature
IR(cm$^{-1}$):2870–3020, 1596, 1497
NMR(CDCl$_3$)δ (ppm):1.21, 3H, t; 1.7–2.1, 2H, m; 2.35, 3H, s; 2.5–2.8, 6H, m; 6.9–7.3, 4H, m; 8.33, 1H, d; 8.37, 1H, s

| Elementary Analysis (%) | | | |
|---|---|---|---|
| | C | H | Cl | N |
| Calculated | 74.58 | 7.36 | 12.95 | 5.11 |
| Found | 74.25 | 7.21 | 13.16 | 5.37 |
| Yield | 9.0% | | | |

Compound 89

| Starting materials: | 3,4-dimethyl-5-ethylpyridine | (1.26 g) |
|---|---|---|
| | 1-bromo-2-phenylethane | (1.73 g) |
| Product: | 1-phenyl-3-(3-ethyl-5-methyl-4-pyridyl)-propane | (compound 89) |

Oily substance at room temperature
IR(cm$^{-1}$):2890–3070, 1593, 1502
NMR(CDCl$_3$)δ (ppm):1.17, 3H, t; 1.7–2.9, 2H, m; 2.19, 3H, s; 2.4–2.9, 6H, m; 7.1–7.4, 5H, m; 8.16, 1H, s; 8.19, 1H, s

| Elementary Analysis (%) | | | |
|---|---|---|---|
| | C | H | N |
| Calculated | 85.31 | 8.84 | 5.85 |
| Found | 85.64 | 8.48 | 5.86 |

-continued

| | Elementary Analysis (%) | | |
|---|---|---|---|
| | C | H | N |
| Yield | 42.4% | | |

EXAMPLE 47

The pyridine derivatives of the compounds 90 to 92 were obtained in the same manner as in Example 26 by using the compounds shown below as the starting materials. Compound 90

| Starting materials: | 3,4-dimethyl-5-ethylpridine | (1.26 g) |
|---|---|---|
| | 1-bromo-3-phenylpropane | (1.86 g) |
| Product: | 1-phenyl-4-(3-methyl-5-ethyl-4-pyridyl)-butane | (compound 90) |

Oily substance at room temperature
IR(cm$^{-1}$):2880–3040, 1595, 1502
NMR(CDCl$_3$)δ (ppm):1.19, 3H, t; 1.35–2.9, 4H, m; 2.23, 3H, s; 2.4–2.8, 6H, m; 7.0–7.4, 5H, m; 8.17, 1H, s; 8.20, 1H, s

| | Elementary Analysis (%) | | |
|---|---|---|---|
| | C | H | N |
| Calculated | 86.01 | 8.42 | 5.57 |
| Found | 85.92 | 8.25 | 5.83 |
| Yield | 59.4% | | |

Compound 91

| Starting materials: | 3,4-dimethyl-5-n-propylpyridine | (1.39 g) |
|---|---|---|
| | 1-bromo-3-phenylpropane | (1.86 g) |
| Product: | 1-phenyl-4-(3-methyl-5-n-propyl-4-pyridyl)-butane | (compound 91) |

Oily substance at room temperature
IR(cm$^{-1}$):2900–3100, 1603, 1512
NMR(CDCl$_3$)δ (ppm):0.97, 3H, t; 1.3–2.1, 6H, m; 2.25, 3H, s; 2.4–2.8, 6H, m; 7.1–7.4, 5H, m; 8.18, 2H, s

| | Elementary Analysis (%) | | |
|---|---|---|---|
| | C | H | N |
| Calculated | 85.34 | 9.43 | 5.23 |
| Found | 85.65 | 9.36 | 4.97 |
| Yield | 38.3% | | |

Compound 92

| Starting materials: | 3-ethyl-4-methyl-5-n-butylpridine | (1.65 g) |
|---|---|---|
| | 1-bromo-3-phenylpropane | (1.86 g) |
| Product: | 1-phenyl-4-(3-ethyl-5-n-butyl-4-pyridyl)-butane | (compound 92) |

Oily substance at room temperature
IR(cm$^{-1}$):2870–3070, 1586, 1498
NMR(CDCl$_3$)δ (ppm):0.94, 3H, t; 1.21, 3H, t; 1.2–2.9, 8H, m; 2.3–2.8, 8H, m; 7.0–7.4, 5H, m; 8.19, 2H, s

| | Elementary Analysis (%) | | |
|---|---|---|---|
| | C | H | N |
| Calculated | 85.37 | 9.89 | 4.74 |
| Found | 84.96 | 10.28 | 4.78 |
| Yield | 11.2% | | |

EXAMPLE 48

The pyridine derivatives of the compound 93 to 97 were obtained in the same manner as in Example 18 by using the compounds shown below were used as the starting material and the alkylating agent.
Compound 93

| Starting material: 1-phenyl-4-(3-ethyl-4-pyridyl)-butane | (2.0 g) |
|---|---|
| Alkylating agent: ethyl iodide | (1.30 g) |
| Product: 1-phenyl-4-(3-ethyl-4-pyridyl)-hexane | (compound 93) |

Oily substance at room temperature
IR(cm$^{-1}$):2900–3100, 1606, 1508
NMR(CDCl$_3$)δ (ppm):0.77, 3H, t; 1.20, 3H, t; 1.35–1.9, 6H, m; 2.4–3.0, 5H, m; 7.01, 1H, d; 7.05–7.4, 5H, m; 8.34, 1H, d; 8.35, 1H, s

| | Elementary Analysis (%) | | |
|---|---|---|---|
| | C | H | N |
| Calculated | 85.34 | 9.43 | 5.23 |
| Found | 85.30 | 9.44 | 5.28 |
| Yield | 18.7% | | |

Compound 94

| Starting material: 1-phenyl-4-(3-ethyl-4-pyridyl)-butane | (2.0 g) |
|---|---|
| Alkylating agent: isobutyl bromide | (1.15 g) |
| Product: 1-phenyl-4-(3-ethyl-4-pyridyl)-6-methylheptane | (compound 94) |

Oily substance at room temperature
IR(cm$^{-1}$):2890–3080, 1601, 1503
NMR(CDCl$_3$)δ (ppm):0.83, 3H, d; 0.85, 3H, d; 1.21, 3H, t; 1.35–1.8, 7H, m; 2.4–3.1, 5H, 7.02, 1H, d; 7.05–7.4, 5H, m; 8.34, 1H, d; 8.35, 1H, s

| | Elementary Analysis (%) | | |
|---|---|---|---|
| | C | H | N |
| Calculated | 85.37 | 9.89 | 4.74 |
| Found | 85.52 | 9.72 | 4.74 |
| Yield | 8.5% | | |

Compound 95

| Starting materials: 1-phenyl-4-(3-methyl-4-pyridyl)-pentane | (2.0 g) |
|---|---|
| Alkylating agent: ethyl iodide | (1.30 g) |
| Product: 1-phenyl-4-(3-n-propyl-4-pyridyl)-pentane | (compound 95) |

Oily substance at room temperature
IR(cm$^{-1}$):2890–3080, 1600, 1502

NMR(CDCl$_3$)δ (ppm):0.97, 3H, t; 1.19, 3H, d; 1.25-1.9, 6H, m; 2.2-3.15, 5H, m; 7.05, 1H, d; 7.1-7.5, 5H, m; 8.32, 1H, s; 8.34, 1H, d

| | Elementary Analysis (%) | | |
|---|---|---|---|
| | C | H | N |
| Calculated | 85.34 | 9.43 | 5.23 |
| Found | 85.12 | 9.67 | 5.22 |
| Yield | 18.3% | | |

Compound 96

| Starting material: 1-phenyl-4-(3-methyl-4-pyridyl)-pentane | (2.0 g) |
|---|---|
| Alkylating agent: isopropyl iodide | (1.42 g) |
| Product: 1-phenyl-4-(3-i-butyl-4-pyridyl)-pentane | (compound 96) |

Oily substance at room temperature
IR(cm$^{-1}$):2890-3090, 1601, 1505
NMR(CDCl$_3$)δ (ppm):0.90, 3H, d; 0.91, 3H, d; 1.18, 3H, d; 1.3-1.9, 5H, m; 2.3-3.1, 5H, m; 7.05, 1H, d; 7.1-7.4, 5H, m; 8.27, 1H, s; 8.35, 1H, d

| | Elementary Analysis (%) | | |
|---|---|---|---|
| | C | H | N |
| Calculated | 85.36 | 9.67 | 4.97 |
| Found | 84.94 | 9.85 | 5.21 |
| Yield | 35.9% | | |

Compound 97

| Starting material: 1-phenyl-3-(3-ethyl-4-pyridyl)-propane | (2.1 g) |
|---|---|
| Alkylating agent: isobutyl bromide | (1.28 g) |
| Product: 1-phenyl-3-(3-ethyl-4-pyridyl)-5-methylhexane | (Compound 97) |

Oily substance at room temperature
IR(cm$^{-1}$):2900-3090, 1602, 1506
NMR(CDCl$_3$)δ (ppm):0.85, 3H, d; 0.87, 3H, d; 1.17, 3H, t; 1.3-2.1, 5H, m; 2.3-2.7, 4H, m; 2.8-3.2, 1H, m; 6.95-7.4, 6H, m; 8.38, 1H, s; 8.44, 1H, d

| | Elementary Analysis (%) | | |
|---|---|---|---|
| | C | H | N |
| Calculated | 85.36 | 9.67 | 4.97 |
| Found | 85.44 | 9.71 | 4.83 |
| Yield | 31.8% | | |

EXAMPLE 49

Preparation of 1-(4-t-butylphenyl)-3-(3-ethyl-4-pyridyl)propane

In a flask, 2.75 g (20.6 mmol) of anhydrous alminum chloride and 4 ml of dried nitromethane were placed and the mixture was cooled on an ice bath wherein salt had been added. A solution of 2.1 g (9.35 mmol) of 1-phenyl-3-(3-ethyl-4-pyridyl)-propane dissolved in nitromethane was added thereto and the resulting mixture was stirred for 30 minutes, and further a solution of 2.3 g (10 mmol) of 2,6-di-t-butyl-cresol dissolved in nitromethane was added dropwise. After stirring for one hour at not higher than 0° C., the ice bath was removed and stirred for one hour at room temperature. After completion of the reaction, water was added and the mixture was extracted with ethyl acetate. After drying over anhydrous sodium sulfate, the solvent was distilled away under reduced pressure and the resulting oily substance was purified by silica gel column chromatography, to obtain 0.85 g (yield: 34.0%) of the desired compound.

The resulting compound was identified as 1-(4-t-butylphenyl)-3-(3-ethyl-4-pyridyl)-propane (hereinafter referred to as compound 98) by the analytical results shown below.

Oily substance at room temperature
IR(cm$^{-1}$):2890-3070, 1600, 1519
NMR(CDCl$_3$)δ (ppm):1.18, 3H, t; 1.32, 9H, s; 1.8-2.1, 2H, m; 2.45-2.8, 6H, m; 7.03, 1H, d; 7.12, 2H, d; 7.32, 2H, d; 8.32, 1H, d; 8.36, 1H, s

| | Elementary Analysis (%) | | |
|---|---|---|---|
| | C | H | N |
| Calculated | 85.36 | 9.67 | 4.97 |
| Found | 85.10 | 9.82 | 5.08 |

EXAMPLE 50

Preparation of 1-phenyl-2-methyl-4-(3-ethyl-4-pyridyl)pentane 1.2 g (4.53 mmol) of 1-phenyl-2-methyl-4-(3-ethyl-4-pyridyl)-1-pentene (Compound 63) obtained in Example 46 was dissolved in 30 ml of methanol, 250 mg of 5% palladium carbon was added thereto and the resulting mixture was stirred for 8 hours at room temperature in an atmosphere of hydrogen. Palladium-carbon was filtered out and methanol was distilled away under reduced pressure, to obtain 1.1 g (yield: 91.2%) of the desired compound.

The resulting compound was identified as 1-phenyl-2-methyl-4-(3-ethyl-4-pyridyl)-pentane (hereinafter referred to as compound 99) by the analytical results shown below.

Oily substance at room temperature
IR(cm$^{-1}$):2900-3080, 1600, 1500
NMR(CDCl$_3$)δ (ppm)0.86, 3H, d; 1.19, 3H, t; 1.4-1.9, 3H, m; 2.2-3.3, 5H, m; 6.9-7.4, 6H, m; 8.26, 1H, d; 8.34, 1H, s

| | Elementary Analysis (%) | | |
|---|---|---|---|
| | C | H | N |
| Calculated | 85.34 | 9.43 | 5.23 |
| Found | 85.46 | 9.41 | 5.12 |

EXAMPLE 51

The procedure of Example 50 was repeated with the exception that 1.2 g of 1-(3-ethyl-4-pyridyl)-2-methyl-4-phenyl-1-butene (compound 55) obtained in Example 42 was used in place of 1-phenyl-2-methyl-4-(3-ethyl-4-pyridyl)-1-pentene in Example 50, to obtain 0.95 g (yield: 78.4%) of 1-(3-ethyl-4-pyridyl)-2-methyl-4-phenylbutane (hereinafter referred to as compound 100).

Oily substance at room temperature
IR(cm$^{-1}$):2900-3090, 1606, 1510
NMR(CDCl$_3$)δ (ppm):0,93, 3H, d; 1.19, 3H, t; 1.4-2.0, 3H, m; 2.2-2.9, 6H, m; 6.96, 1H, d; 7.0-7.45, 5H, m; 8.29, 1H, d; 8.35, 1H, s

| Elementary Analysis (%) | | | |
|---|---|---|---|
| | C | H | N |
| Calculated | 85.33 | 9.15 | 5.52 |
| Found | 85.11 | 9.02 | 5.87 |

EXAMPLE 52

1.5 g (5.88 mmol) of 1-(3-ethyl-4-pyridyl)-4-phenyl-2-butanol and 4 g (33.6 mmol) of thionyl chloride were mixed and stirred for 2 hours at room temperature. After completion of the reaction, excessive thionyl chloride was distilled away under reduced pressure and water was added. The resulting mixture was made basic with sodium carbonate and extracted with ethyl acetate. The extract was washed with saturated brine, then dried over anhydrous sodium sulfate. Ethyl acetate was distilled away under reduced pressure and the resulting oily substance was purified by silica gel column chromatography, to obtain 1.52 g (yield: 95.1%) of the desired compound.

The resulting compound was identified as 1-(3-ethyl-4-pyridyl)-2-chloro-4-phenylbutane (hereinafter referred to as compound 101) by the analytical results shown below.

Oily substance at room temperature
IR(cm$^{-1}$):2880–3060, 1597, 1500
NMR(CDCl$_3$)$\delta$ (ppm):1.08, 3H, t; 1.99, 2H, dt; 2.53, 2H, q; 2.77, 2H, q; 2.97, 2H, d; 3.95, 1H, m; 6.95, 1H, d; 7.0–7.4, 5H, m; 8.27, 1H, d; 8.30, 1H, s

| Elementary Analysis (%) | | | | |
|---|---|---|---|---|
| | C | H | Cl | N |
| Calculated | 74.58 | 7.36 | 12.95 | 5.11 |
| Found | 74.94 | 7.09 | 12.74 | 5.21 |

EXAMPLE 53

3.0 g (11.8 mmol) of 1-(3-ethyl-4-pyridyl)-2-methyl-3-phenyl-2-propanol was cooled to 0° C., and while stirring, 3 ml of thionyl chloride was added thereto. The resulting mixture was stirred for one hour, then the temperature was returned to room temperature and the mixture was kept stirring for another one hour. Excessive thionyl chloride was distilled away under reduced pressure, a saturated sodium bicarbonate solution was added thereto and the mixture was extracted with ethyl acetate. Subsequently, the extract was dried over anhydrous sodium sulfate, then ethyl acetate was distilled away under reduced pressure, to obtain 2.1 g (yield: 75%) of a mixture of 1-phenyl-2-methyl-3-(3-ethyl-4-pyridyl)-1-propene and 1-(3-ethyl-4-pyridyl)-2-methyl-3-phenyl-1-propene.

Subsequently, 2.1 g of this mixture was dissolved in 20 ml of a solution of ethyl alcohol and acetic acid in the ratio 1:1 and 500 mg of 5% palladium-carbon was added thereto. The resulting mixture was stirred for 6 hours in an atmosphere of hydrogen. After the resulting solution was filtered and washed with ethyl alcohol, the filtrate and the washed solution were mixed, and the solvent was distilled away under reduced pressure. The residue was dissolved in ethyl acetate, washed with 5% sodium hydroxide and then dried over anhydrous sodium sulfate. The solvent was distilled away under reduced pressure, to obtain 2.1 g (yield: 98.6%) of the desired compound.

The resulting compound was identified as 1-(3-ethyl-4-pyridyl)-2-methyl-3-phenylpropane (hereinafter referred to as compound 102) by the analytical results shown below.

Oily substance at room temperature
IR(cm$^{-1}$):2890–3070, 1608, 1500
NMR(CDCl$_3$)$\delta$ (ppm):0.88, 3H, d; 1.16, 2H, t; 2.4–2.9, 6H, m d; 7.0–7.4, 6H, m; 8.36, 1H, d; 8.39, 1H, s

| Elementary Analysis (%) | | | |
|---|---|---|---|
| | C | H | N |
| Calculated | 85.31 | 8.84 | 5.85 |
| Found | 85.25 | 8.72 | 6.02 |

EXAMPLE 54

The compound obtained in Example 41 was reacted with hydrochloric acid and oxalic acid, to obtain hydrochloride of (E, E)-1-phenyl-4-(3-ethyl-4-pyridyl)-1,3-butadiene (hereinafter referred to as compound 103) and oxalate of (E, E)-1-phenyl-4-(3-ethyl-4-pyridyl)-1,3-butadiene (hereinafter referred to as compound 104). The melting point of these compounds were 152.1° to 152.9° C. and 181.2° to 182.7° C. respectively.

TEST EXAMPLE 1

Effect on *Nilaparvata lugens*

Into the chemical solution of each test compound in prescribed concentration (500 ppm), a stem of paddy rice plant cut out in the length of 10 cm was dipped for one minute, air-dried, and put into test tube containing water. Then larvae (third instar) of *Nilaparvata lugens* were left free into the test tube, a cotton plug was applied, and let stand in an incubating chamber at 25° C. Seven days after the treatment, when the larvae were examined for viability, it was found that 100% of mortality of larvae was accomplished in all the test compounds (compounds 1 to 104).

INDUSTRIAL APPLICABILITY

As described above, the novel pyridine derivatives of the present invention and the salts thereof exhibit a strong insecticidal and miticidal activity. Consequently, according to the present invention, an excellent insecticide and miticide containing a novel pyridine derivative and the salt thereof can be provided. In addition, since the insecticide and miticide of the present invention is different in structure from the conventionally known ones, it is also different in activity, and especially exhibits a remarkable effect for the control of noxious insects which have acquired resistance to conventional insecticides. Moreover, it is rapid in decomposition, and is decomposed immediately after application, so it is free from the fear of causing problems of residuality or accumulativity.

Therefore, the insecticide and miticide of the present invention is expected to be utilized effectively and extensively for the control of pests in agriculture and horticulture.

We claim:
1. A pyridine compound of the formula:

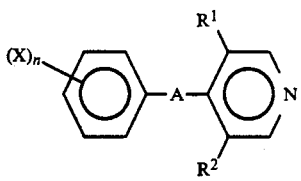

wherein
X is a hydrogen atom, a halogen atom selected from the group consisting of chlorine, fluorine, bromine and iodine; an alkyl group selected from the group consisting of methyl, ethyl, n-propyl, isopropyl, n-butyl, isobutyl, s-butyl, and t-butyl; an alkoxyl group selected from the group consisting of methoxyl, ethoxyl, n-propoxyl, isopropyl, n-butoxyl, isobutoxyl and t-butoxyl; or a haloalkyl group selected from the group consisting of monochloromethyl, dichloromethyl, trichloromethyl, monochloroethyl, dichloroethyl, trichloroethyl, tetrachloroethyl, monochloropropyl, dichloropropyl, trichloropropyl, tetrachloropropyl, pentachloropropyl, monochlorobutyl, dichlorobutyl, trichlorobutyl, tetachlorobutyl, pentachlorobutyl and hexachlorobutyl, n is an integer of 1 to 5, and when n is 2 or more, the groups are identical to or different from each other, A is selected from the group consisting of propyl, butyl, pentyl, hexyl, heptyl, octyl, 8-methyloctyl, 1-propene, 1-butene, 2-butene, 1-pentene, 2-hexene, 1-heptene, 2-heptene, 1-octene, 2-octene, 1,3-butadiene, 1,3-pentadiene, 1,4-pentadiene, 1,3-hexadiene, 2,4-hexadiene, 1,4-hexadiene, 1,3-heptadiene, 2,4-heptadiene, 1,3-octadiene and 2,4-octadiene, $R^1$ is a hydrogen atom or an alkyl group selected from the group consisting of methyl, ethyl, n-propyl, isopropyl, n-butyl, isobutyl, s-butyl, t-butyl, n-pentyl, isopentyl, neopentyl, t-pentyl, n-hexyl and isohexyl, and $R^2$ is an alkyl group selected from the group consisting of methyl, ethyl, n-propyl, isopropyl, n-butyl, isobutyl, s-butyl, t-butyl, n-pentyl, isopentyl, neopentyl, t-pentyl, n-hexyl and isohexyl, or salts of said pyridine compound, said salts being salts of hydrochloric acid, hydrobromic acid, hydroiodic acid, hydrofluoric acid, sulfuric acid, phosphoric acid, nitric acid, citric acid, lactac acid, oxalic acid, maleic acid, tartaric acid, benzoic acid, nicotinic acid or dodecylbenzene sulfonic acid.

2. The pyridine compound or a salt thereof as defined in claim 1, wherein the pyridine compound is of the formula (I'):

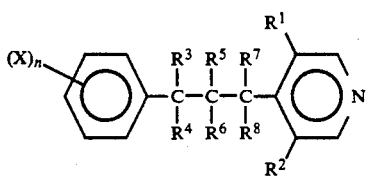

wherein $R^3$ to $R^8$ are the same or different and are a hydrogen atom, an alkyl group having 1 to 4 carbon atoms or a halogen atom.

3. The pyridine compound or a salt thereof as defined in claim 1, wherein the pyridine compound is of the formula (I''):

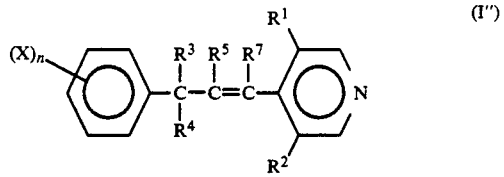

wherein $R^3$, $R^4$, $R^5$ and $R^7$ are the same or different and are an hydrogen atom, an alkyl group having 1 to 4 carbon atoms or a halogen atom.

4. The pyridine compound or a salt thereof as defined in claim 1, wherein the pyridine compound is of the formula (I'''):

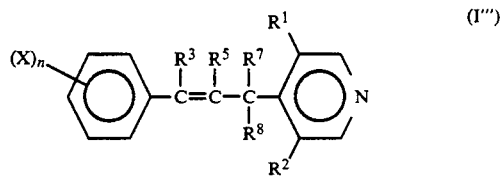

wherein $R^3$, $R^5$, $R^7$ and $R^8$ are the same or different and are a hydrogen atom, an alkyl group having 1 to 4 carbon atoms or a halogen atom.

5. The pyridine compound or a salt thereof as defined in claim 1, wherein the pyridine compound is of the formula (I''''):

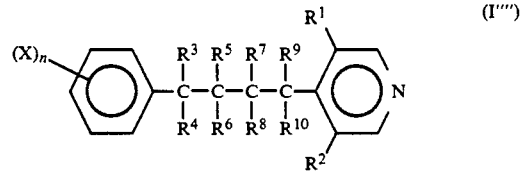

wherein $R^3$, $R^4$, $R^5$, $R^6$, $R^7$, $R^8$, $R^9$ and $R^{10}$ are the same or different and are a hydrogen atom, an alkyl group having 1 to 4 carbon atoms or a halogen atom.

6. An insecticide or miticide composition comprising as an active ingredient, an effective insecticidal or miticidal amount of the pyridine compound or said salt thereof according to claim 1 and a carrier.

7. The insecticide and miticide composition as defined in claim 6, wherein the pyridine compound is a compound of the formula (I'):

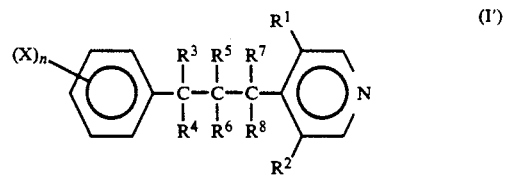

wherein $R^3$ to $R^8$ are the same or different and are a hydrogen atom, an alkyl group having 1 to 4 carbon atoms or a halogen atom, or said salt of the pyridine compound.

8. The insecticide and miticide composition as defined in claim 6, wherein the pyridine compound is a compound of the formula (I''):

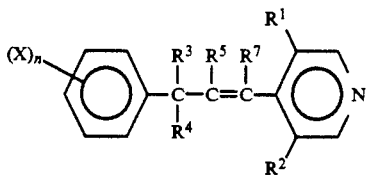

wherein R³, R⁴, R⁵ and R⁷ are the same or different and are a hydrogen atom, an alkyl group having 1 to 4 carbon atoms or a halogen atom, or said salt of the pyridine compound.

9. The insecticide and miticide composition as defined in claim 6, wherein the pyridine compound is a compound of the formula (I'''):

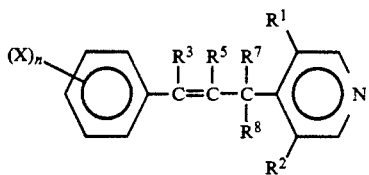

wherein R³, R⁵, R⁷ and R⁸ are the same or different and are a hydrogen atom, an alkyl group having 1 to 4 carbon atoms or a halogen atom, or said salt of the pyridine compound.

10. The insecticide and miticide composition as defined in claim 6, wherein the pyridine compound is a compound of the formula (I''''):

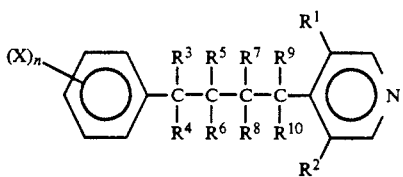

wherein R³, R⁴, R⁵, R⁶, R⁷, R⁸, R⁹ and R¹⁰ are the same or different and are hydrogen atom, an alkyl group having 1 to 4 carbon atoms or a halogen atom, or said salt of the pyridine compound.

11. A method of combatting insects or mites comprising applying to insects or to a locus thereof an effective insecticidal or miticidal amount of the pyridine compound or said salt thereof according to claim 1.

12. The method defined in claim 11 wherein the compound is of the formula (I'):

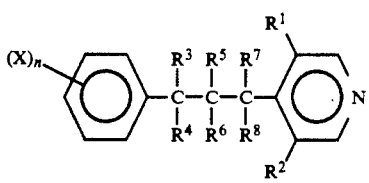

wherein R³ to R⁸ are the same or different and are a hydrogen atom, an alkyl group having 1 to 4 carbon atoms or a halogen atom, or said salt of the pyridine compound.

13. The method defined in claim 11, wherein the compound is of the formula (I''):

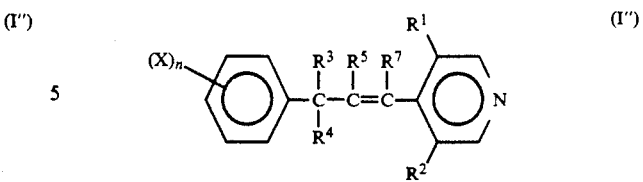

wherein R³, R⁴, R⁵, and R⁷ are the same or different and a hydrogen atom, are an alkyl group having 1 to 4 carbon atoms or a halogen atom, or said salt of the pyridine compound.

14. The method defined in claim 11, wherein the compound is of the formula (I'''):

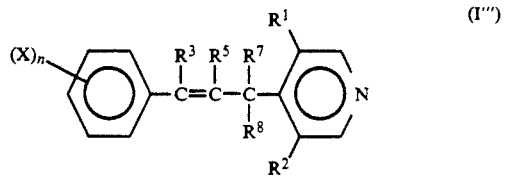

wherein R³, R⁵, R⁷ and R⁸ are the same or different and are a hydrogen atom, an alkyl group having 1 to 4 carbon atoms or a halogen atom, or said salt of the pyridine compound.

15. The method defined in claim 11, wherein the compound is of the formula (I''''):

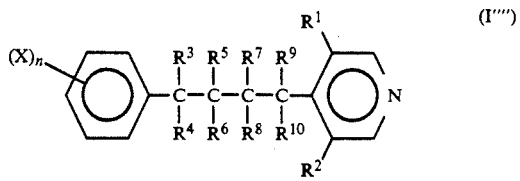

wherein R³, R⁴, R⁵, R⁶, R⁷, R⁸, R⁹ and R¹⁰ are the same or different and are a hydrogen atom, an alkyl group having 1 to 4 carbon atoms or a halogen atom, or said salt of the pyridine compound.

16. The pyridine compound as defined in claim 1, wherein said compound is selected from the group consisting of 1-phenyl-3-(3-ethyl-4-pyridyl)-propane, 1-phenyl-3-(3-ethyl-4-pyridyl)butane, 1-phenyl-3-(3-methyl-4-pyridyl)-propane, 1-(2-chlorophenyl)-3-(3-ethyl-4-pyridyl)-propane, 1-(3-chlorophenyl)-3-(3-ethyl-4-pyridyl)-propane, 1-phenyl-3-(3-methyl-4-pyridyl)-butane, 1-phenyl-3-(3-n-propyl-4-pyridyl)-butane, 1-phenyl-3-(3-n-butyl-4-pyridyl)-butane, 1-phenyl-3-(3-isobutyl-4-pyridyl)-butane, 1-phenyl-3-(3-n-hexyl-4-pyridyl)-butane, 1-(2-methylphenyl)-3-(3-ethyl-4-pyridyl)-propane ,1-(3-methylphenyl)-3-(3-ethyl-4-pyridyl)-propane, 1-(4-t-butylphenyl-3-(3-ethyl-4-pyridyl)-propane, 1-(3-ethyl-4-pyridyl)3-phenylbutane, 1-(3-chloro-4-methylphenyl)-3-(3-ethyl-4-pyridyl)-propane, 1-phenyl-3-(3-ethyl-4-pyridyl)-5-methylhexane, 1-phenyl-2-methyl-3-(3-ethyl-4-pyridyl)-propane, 1-phenyl-4-(3-methyl-4-pyridyl)-butane, 1-phenyl-4-(3-ethyl-4-pyridyl)-butane, 1-phenyl-4-(3-methyl-4-pyridyl)-pentane, 1-(2-chlorophenyl)-4-(3-ethyl-4-pyridyl)-butane, 1-(3-chlorophenyl)-4-(3-ethyl-4-pyridyl)-butane, 1-(4-chlorophenyl)-4-(3-ethyl-4-pyridyl)-butane, 1-(3-chlorophenyl)-4-(3-methyl-4-pyridyl)-butane, 1-(3,4-dichlorophenyl)-4-(3-ethyl-4-pyridyl)-butane, 1-(3,4-dichlorophenyl)-4-(3-methyl -4-pyridyl)-pentane, 1-(3-trifluoromethylphenyl)-4-(3-ethyl-4-pyridyl)-butane, 1-(3-trifluoromethylphenyl)-4-(3-methyl-4-pyridyl)-pentane, 1-(4-t-butylphenyl)-4-(3-ethyl-4-pyridyl)-butane, 1-phenyl-4-(3-n-propyl-4-pyridyl)-pentane, 1-phenyl-4-(3-i-butyl-4-pyridyl)-pentane, 1-phenyl-4-(3-ethyl-4-pyridyl)-hexane, 1-phenyl-4-(3-ethyl-4-pyridyl)-pentane, 1-phenyl-2-methyl-4-(3-ethyl-4-pyridyl)-1-butene, 1-phenyl-2-methyl-4-(3-ethyl-4-pyridyl)-butane, 1-phenyl-2-methyl-4-(3-ethyl-4-pyridyl)-pentane, 1-(2-methylphenyl)-4-(3-ethyl-4-pyridyl)-butane, 1-(3-methylphenyl)-4-(3-ethyl-4-pyridyl)-butane, 1-(4-methylphenyl)-4-(3-ethyl-4-pyridyl)-butane, 1-(3-chloro-4-methylphenyl)-4-(3-ethyl-4-pyridyl)-butane, 1-phenyl-4-(3-methyl-4-pyridyl)-pentane, 1-(3-ethyl-4-pyridyl)-4-phenylpentane, 2-phenyl-3-methyl-5-(3-ethyl-4-pyridyl)-hexane, 1-phenyl-3-methyl-4-(3-ethyl-4-pyridyl)-butane, 1-phenyl-4-(3-ethyl-4-pyridyl)-butane, 1-phenyl-4-(3-ethyl-4-pyridyl)-hexane, 1-phenyl-3-chloro-4-(3-ethyl-4-pyridyl)-butane, 1-phenyl-3-methyl-4-(3-ethyl-4-pyridyl)-1,3-butadiene, 1-phenyl-4-(3-ethyl-5-methyl-4-pyridyl)-butane, 1-phenyl-4-(3-methyl-5-propyl-4-pyridyl)-butane, 1-phenyl-5-(3-methyl-4-pyridyl)-pentane, 1-phenyl-5-(3-ethyl-4-pyridyl)-pentane, 1-phenyl-5-(3-methyl-4-pyridyl)-hexane, 1-(2-chlorophenyl)-5-(3-ethyl-4-pyridyl)-pentane, 1-(3-chlorophenyl)-5-(3-ethyl-4-pyridyl)-pentane, 1-(4-chlorophenyl)-5-(3-ethyl-4-pyridyl)-pentane, 1-phenyl-6-(3-ethyl-4-pyridyl)-hexane, 1-phenyl-7-(3-ethyl-4-pyridyl)-heptane, 1-phenyl-8-(3-ethyl-4-pyridyl)-octane and 1-phenyl-8-(3-ethyl-4-pyridyl)-nonane.

17. The composition as defined in claim 6, wherein said compound is selected from the group consisting of 1-phenyl-3-(3-ethyl-4-pyridyl)-propane, 1-phenyl-3-(3-ethyl-4-pyridyl)-butane, 1-phenyl-3-(3-methyl-4-pyridyl)-propane, 1-(2-chlorophenyl-3-(3-ethyl-4-pyridyl)-propane, 1-(3-chlorophenyl)-3-(3-ethyl-4-pyridyl)-propane, 1-phenyl-3-(3-methyl-4-pyridyl)-butane, 1-phenyl-3-(3-n-propyl-4-pyridyl)-butane, 1-phenyl-3-(3-n-butyl-4-pyridyl)-butane, 1-phenyl-3-(3-isobutyl-4-pyridyl)-butane, 1-phenyl-3-(3-n-hexyl-4-pyridyl)-butane, 1-(2-methylphenyl)-3-(3-ethyl-4-pyridyl)-propane, 1-(3-methylphenyl)-3-(3-ethyl-4-pyridyl)-propane, 1-(4-t-butylphenyl-3-(3-ethyl-4-pyridyl)-propane, 1-(3-ethyl-4-pyridyl)-3-phenylbutane, 1-(3-chloro-4-methylphenyl)-3-(3-ethyl-4-pyridyl)-propane, 1-phenyl-3-(3-ethyl-4-pyridyl)-5-methylhexane, 1-phenyl-2-methyl-3-(3-ethyl-4-pyridyl)-propane, 1-phenyl-4-(3-methyl-4-pyridyl)-butane, 1-phenyl-4-(3-ethyl-4-pyridyl)-butane, 1-phenyl-4-(3-ethyl-4-pyridyl)-pentane, 1-(2-chlorophenyl)-4-(3-ethyl-4-pyridyl)-butane, 1-(3-chlorophenyl)-4-(3-ethyl-4-pyridyl)-butane, 1-(4-chlorophenyl)-4-(3-ethyl-4-pyridyl)-butane, 1-(3-chlorophenyl)-4-(3-methyl-4-pyridyl)-butane, 1-(3,4-dichlorophenyl)-4-(3-ethyl-4-pyridyl)-butane, 1-(3,4-dichlorophenyl)-4-(3-methyl-4-pyridyl)-pentane, 1-(3-trifluoromethylphenyl)-4-(3-ethyl-4-pyridyl)-butane, 1-(3-trifluoromethylphenyl)-4-(3-methyl-4-pyridyl)-pentane, 1-(4-t-butylphenyl)-4-(3-ethyl-4-pyridyl)-butane, 1-phenyl-4-(3-n-propyl-4-pyridyl)-pentane, 1-phenyl-4-(3-i-butyl-4-pyridyl)-pentane, 1-phenyl-4-(3-ethyl-4-pyridyl)-hexane, 1-phenyl-4-(3-ethyl-4-pyridyl)-pentane, 1-phenyl-2-methyl-4-(3-ethyl-4-pyridyl)-1-butene, 1-phenyl-2-methyl-4-(3-ethyl-4-pyridyl)-butane, 1-phenyl-2-methyl-4-(3-ethyl-4-pyridyl)-pentane, 1-(2-methylphenyl)-4-(3-ethyl-4-pyridyl)-butane, 1-(3-methylphenyl)-4-(3-ethyl-4-pyridyl)-butane, 1-(4-methylphenyl)-4-(3-ethyl-4-pyridyl)-butane, 1-(3-chloro-4-methylphenyl)-4-(3-ethyl-4-pyridyl)-butane, 1-phenyl-4-(3-methyl-4-pyridyl)-pentane, 1-phenyl-3-methyl-5-(3-ethyl-4-pyridyl)-hexane, 1-phenyl-3-methyl-4-(3-ethyl-4-pyridyl)-butane, 1-phenyl-4-(3-ethyl-4-pyridyl)-butane, 1-phenyl-4-(3-ethyl-4-pyridyl)-hexane, 1-phenyl-3-chloro-4-(3-ethyl-4-pyridyl)-butane, 1-phenyl-3-methyl-4-(3-ethyl-4-pyridyl)-1,3-butadiene, 1-phenyl-4-(3-ethyl-5-methyl-4-pyridyl)-butane, 1-phenyl-4-(3-methyl-5-propyl-4-pyridyl)-butane, 1-phenyl-5-(3-methyl-4-pyridyl)-pentane, 1-phenyl-5-(3-ethyl-4-pyridyl)-pentane, 1-phenyl-5-(3-methyl-4-pyridyl)-hexane, 1-(2-chlorophenyl)-5-(3-ethyl-4-pyridyl)-pentane, 1-(3-chlorophenyl)-5-(3-ethyl-4-pyridyl)-pentane, 1-(4-chlorophenyl)-5-(3-ethyl-4-pyridyl)-pentane, 1-phenyl-6-(3-ethyl-4-pyridyl)-hexane, 1-phenyl-7-(3-ethyl-4-pyridyl)-heptane, 1-phenyl-8-(3-ethyl-4-pyridyl)-octane and 1-phenyl-8-(3-ethyl-4-pyridyl)-nonane.

18. The method as defined in claim 11, wherein the compound is selected from the group consisting of 1-phenyl-3-(3-ethyl-4-pyridyl)-propane, 1-phenyl-3-(3-ethyl-4-pyridyl)-butane, 1-phenyl-3-(3-methyl-4-pyridyl)-propane, 1-2-chlorophenyl)-3-(3-ethyl-4-pyridyl)-propane, 1-3-chlorophenyl)-3-(3-ethyl-4-pyridyl)-propane, 1-phenyl-3-(3-methyl-4-pyridyl)-butane, 1-phenyl-3-(3-n-propyl-4-pyridyl)-butane, 1-phenyl-3-(3-methyl-4-pyridyl)-butane, 1-phenyl-3-(3-n-butyl-4-pyridyl)-butane, 1-phenyl-3-(3-isobutyl-4-pyridyl)-butane, 1-phenyl-3-(3-n-hexyl-4-pyridyl)-butane, 1-(2-methylphenyl)-3-(3-ethyl-4-pyridyl)-propane, 1-(3-methylphenyl)-3-(3-ethyl-4-pyridyl)-propane, 1-(4-t-butylphenyl)-3-(3-ethyl-4-pyridyl)-propane, 1-(3-ethyl-4-pyridyl)-3-phenylbutane, 1-(3-chloro-4-methylphenyl)-3-(3-ethyl-4-pyridyl)-propane, 1-phenyl-3-(3-ethyl-4-pyridyl)-5-methylhexane, 1-phenyl-2-methyl-3-(3-ethyl-4-pyridyl)-propane, 1-phenyl-4-(3-methyl-4-pyridyl)-butane, 1-phenyl-4-(3-ethyl-4-pyridyl)-butane, 1-phenyl-4-(3-methyl-4-pyridyl)-pentane, 1-(2-chlorophenyl)-4-(3-ethyl-4-pyridyl)-butane, 1-(3-chlorophenyl)-4-(3-ethyl-4-pyridyl)-butane, 1-(4-chlorophenyl)-4-(3-ethyl-4-pyridyl)-butane, 1-(3-chlorophenyl)-4-(3-methyl-4-pyridyl)-butane, 1-(3,4-dichlorophenyl)-4-(3-ethyl-4-pyridyl)-butane, 1-(3,4-dichlorophenyl)-4-(3-methyl-4-pyridyl)-pentane, 1-(3-trifluoromethylphenyl)-4-(3-ethyl-4-pyridyl)-butane, 1-(3-trifluoromethylphenyl)-4-(3-methyl-4-pyridyl)-pentane, 1-(4-t-butylphenyl)-4-(3-ethyl-4-pyridyl)-butane, 1-phenyl-4-(3-n-propyl-4-pyridyl)-pentane, 1-phenyl-4-(3-i-butyl-4-pyridyl)-pentane, 1-phenyl-4-(3-ethyl-4-pyridyl)-hexane, 1-phenyl-4-(3-ethyl-4-pyridyl)-pentane, 1-phenyl-2-methyl-4-(3-ethyl-4-pyridyl)1-butane, 1-phenyl-2-methyl-4-(3-ethyl-4-pyridyl)-butane, 1-phenyl-2-methyl-4-(3-ethyl-4-pyridyl)-pentane, 1-(2-methylphenyl)-4-(3-ethyl-4-pyridyl)-butane, 1-(3-methylphenyl)-4-(3-ethyl-4-pyridyl)-butane, 1-(3-chloro-4-methylphenyl)-4-(3-ethyl-4-pyridyl)-butane, 1-phenyl-4-(3-methyl-4-pyridyl)-pentane, 1-(3-ethyl-4-pyridyl)-4-phenylpentane, 2-phenyl-3-methyl-5-(3-ethyl-4-pyridyl)-hexane, 1-phenyl;-3-methyl-4-(3-ethyl-4-pyridyl)-butane, 1-phenyl-4-(3-ethyl-4-pyridyl)-butane, 1-phenyl-4-(3-ethyl-4-pyridyl)-hexane, 1-phenyl-3-chloro-4-(3-ethyl-4-pyridyl)-butane, 1-phenyl-3-methyl-4-(3-ethyl-4-pyridyl)-1,3-butadiene, 1-phenyl-4-(3-ethyl-5-methyl-4-pyridyl)-butane, 1-phenyl-4-(3-methyl-5-propyl-4-pyridyl)-butane, 1-phenyl-5-(3-methyl-4-pyridyl)-pentane, 1-phenyl-5-(3-ethyl-4-pyridyl)-pentane, 1-phenyl-5-(3-methyl-4-pyridyl)-hexane, 1-(2-chlorophenyl)-5-(3-ethyl-4-pyridyl)-pentane, 1-(3- chlorophenyl)-5-(3-ethyl-4-pyridyl)-pentane, 1-(4-chlorophenyl)-5-(3-ethyl-4-pyridyl)-pentane, 1-phenyl-6-(3-ethyl-4-pyridyl)-hexane, 1-phenyl-7-(3-ethyl-4-pyridyl)-heptane, 1-phenyl-8-(3-ethyl-4-pyridyl)-octane and 1-phenyl-8-(3-ethyl-4-pyridyl)-nonane.

19. The pyridine compound as defined in claim 1, wherein the salt of the pyridine compound is a hydrochloride or an oxalate.

20. The pyridine compound as defined in claim 1, wherein said compound is selected from the group consisting of
1-phenyl-3-(3-methyl-4pyridyl)-propane;
1-phenyl-3-(3-ethyl-4pyridyl)-propane;
1-phenyl-3-(3-α-butyl-4pyridyl)-butane,
1-phenyl-5-(3-methyl-4pyridyl)-pentane,
1-phenyl-5-(3-ethyl-4pyridyl)-pentane,
1-phenyl-6-(3-ethyl-4pyridyl)-hexane,
(E,E)-1-phenyl-4-(3-ethyl-4pyridyl)-1,3-butadiene,
1-phenyl-4-(3-methyl-4pyridyl)-butane,
1-phenyl-4-(3-ethyl-4pyridyl)-butane,
1-phenyl-3-(3-ethyl-4pyridyl)-propane,
1-(3-ethyl-4pyridyl)-3-phenylbutane,
1-phenyl-3-(3-ethyl-4pyridyl)-5-methylhexane,
1-(3-ethyl-4pyridyl)-2-methyl-3-phenylpropane,
1-phenyl-4-(3-ethyl-4pyridyl)-butene,
(E)-1-phenyl-2-methyl-4-(3-ethyl-4-pyridyl)-1-butane,
(E)-1-phenyl-2-methyl-4-(3-ethyl-4-pyridyl)-1-pentene,
1-(3-ethyl-4-pyridyl)-4-phenylpentane,
1-phenyl-2-methyl-4-(3-ethyl-4-pyridyl)-pentane,
2-phenyl-3-methyl-5-(3-methyl-4-pyridyl)-hexane,
1-(3-ethyl-4-pyridyl)-2-methyl-4-phenylbutane,
(E)-1-(3-ethyl-4-pyridyl)-2-methyl-4-phenyl-1-butane,
(Z)-1-(3-ethyl-4-pyridyl)-2-methyl-4-phenyl-1-butane,
1-phenyl-2-methyl-4-(3-ethyl-4-pyridyl)-butane,
1-phenyl-4-(3-ethyl-4-pyridyl)-hexane,
1-(3-ethyl-4-pyridyl)-2-chloro-4-phenylbutane,
(E,E)-1-(3-ethyl-4-pyridyl)-2-methyl-4-phenyl-1,3-butadiene, and
(Z,E)-1-(3-ethyl-4-pyridyl)-2-methyl-4-phenyl-1,3-butadiene.

* * * * *